(12) United States Patent
Dameron

(10) Patent No.: US 8,163,521 B2
(45) Date of Patent: Apr. 24, 2012

(54) SELF-ASSEMBLED PROTEINS AND RELATED METHODS AND PROTEIN STRUCTURES

(75) Inventor: Charles Dameron, Pittsburgh, PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 0 days.

(21) Appl. No.: 12/912,424

(22) Filed: Oct. 26, 2010

(65) Prior Publication Data

US 2011/0269940 A1    Nov. 3, 2011

Related U.S. Application Data

(60) Division of application No. 11/805,188, filed on May 22, 2007, now Pat. No. 7,879,578, which is a continuation-in-part of application No. 11/751,850, filed on May 22, 2007, now abandoned.

(60) Provisional application No. 60/808,232, filed on May 24, 2006.

(51) Int. Cl.
*C12P 21/06* (2006.01)
*A61K 38/00* (2006.01)

(52) U.S. Cl. ........................... 435/69.7; 530/300

(58) Field of Classification Search .................. None
See application file for complete search history.

(56) References Cited

U.S. PATENT DOCUMENTS 5,948,635 A    9/1999    Kay et al.

OTHER PUBLICATIONS

Cobine, Paul A. et al., "Copper Transfer from the Cu(I) Chaperone, CopZ, to the Repressor, Zn(II)CopY: Metal Coordination Environments and Protein Interactions", Biochemistry 2002, 41, 5822-5829.
Cobine, Paul A. et al., "Role for zinc(II) in the copper(I) regulated protein CopY", Journal of Inorganic Biochemistry 88 (2002) 192-196.
Odermatt, Alex et al., "Two trans-Acting Metalloregulatory Proteins Controlling Expression of the Copper-ATPases of *Enterococcus hirae*", The Journal of Biological Chemistry, vol. 270, No. 9, Issue of Mar. 3, pp. 4349-4354, 1995.
Pazehoski, Kristina O. et al., "Stalking metal-linked dimers", Journal of Inorganic Biochemistry 102 (2008) 522-531.
Brown, Kenneth R. et al., "Structures of the Cuprous-Thiolate Clusters of the Mac1 and Ace1 Transcriptional Activators", Biochemistry 2002, 41, 6469-6476.
Definition of "Multimer" from the Science-Technical Dictionary in Ask.com—see URL <http://www.answers.com/topic/multimer>, Jun. 26, 2009.

*Primary Examiner* — Suzanne M Noakes
(74) *Attorney, Agent, or Firm* — Eckert Seamans Cherin & Mellott, LLC; Carol A. Marmo

(57) ABSTRACT

The present invention provides user-directed construction of novel specific homo- and hetero-dimeric, and multimeric assemblages of proteins. The present invention is comprised of gene sequences that transcribe peptide sequences that form links between proteins, where the peptide sequences produce a hook or loop which supports specific self-assembly of homo-dimers, hetero-dimers and multimers of the proteins to which they are attached. The hook or loop may have a short aliphatic repeat sequence and a metal binding loop. The present invention also provides a method of constructing a hook motif of metal binding loop sequences that may be attached to at least one aliphatic repeat sequence to produce the assemblages of proteins. Also provided are protein structures produced by the methods of the present invention.

10 Claims, 26 Drawing Sheets

(1 of 26 Drawing Sheet(s) Filed in Color)

```
ATLTQEDIQQIMKQINKKEPVETIECNCIPGQCECKKQ    (SEQ ID NO:  2)
LSQTDIIQLQQLITAKAATAPEKVACDCLPNKCDCEKE    (SEQ ID NO:  3)
MTLSDIEKIEALLISKKANAVPEVKCNCIVGQCSCYEH    (SEQ ID NO:  4)
SITEQVSRIDIDDNDMGIGGSETMECKCGMPLCICVAP    (SEQ ID NO:  5)
ISIGKEDDSSPMKNSTVQSTAALIECKCGMPLCICEAP    (SEQ ID NO:  6)
INIGEDDASSPMKNSAIHSAPAVIECKCGMPLCICEAP    (SEQ ID NO:  7)
IYGDAEKPAESGGSQIIRAAARKAACACDQKPCSCSKV    (SEQ ID NO:  8)
IYGDSGKPAEGGGSVISRAATGKVACTCDQKPCNCPKG    (SEQ ID NO:  9)
VPQASIKASDISDFQSVSKINQGKPCTCIGKECQCKRW    (SEQ ID NO: 10)
MSPESITANDISDFQSVSKISQGKPCVCVGKACQCKRW    (SEQ ID NO: 11)
ASPASITISQISDFQSVSIIGTAAECTCDEKECQCKNC    (SEQ ID NO: 12)
```

Figure 2

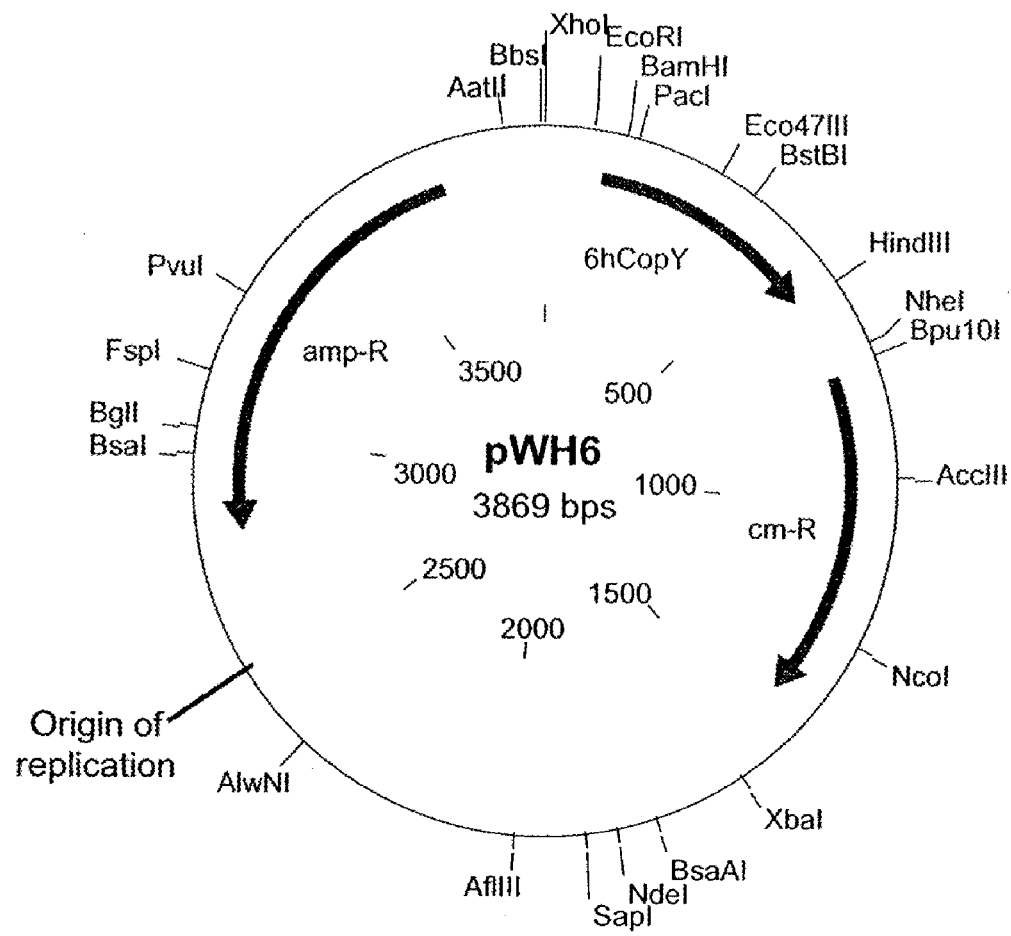
Figure 6. The pWH6 construct for the expression of 6xhis CopY

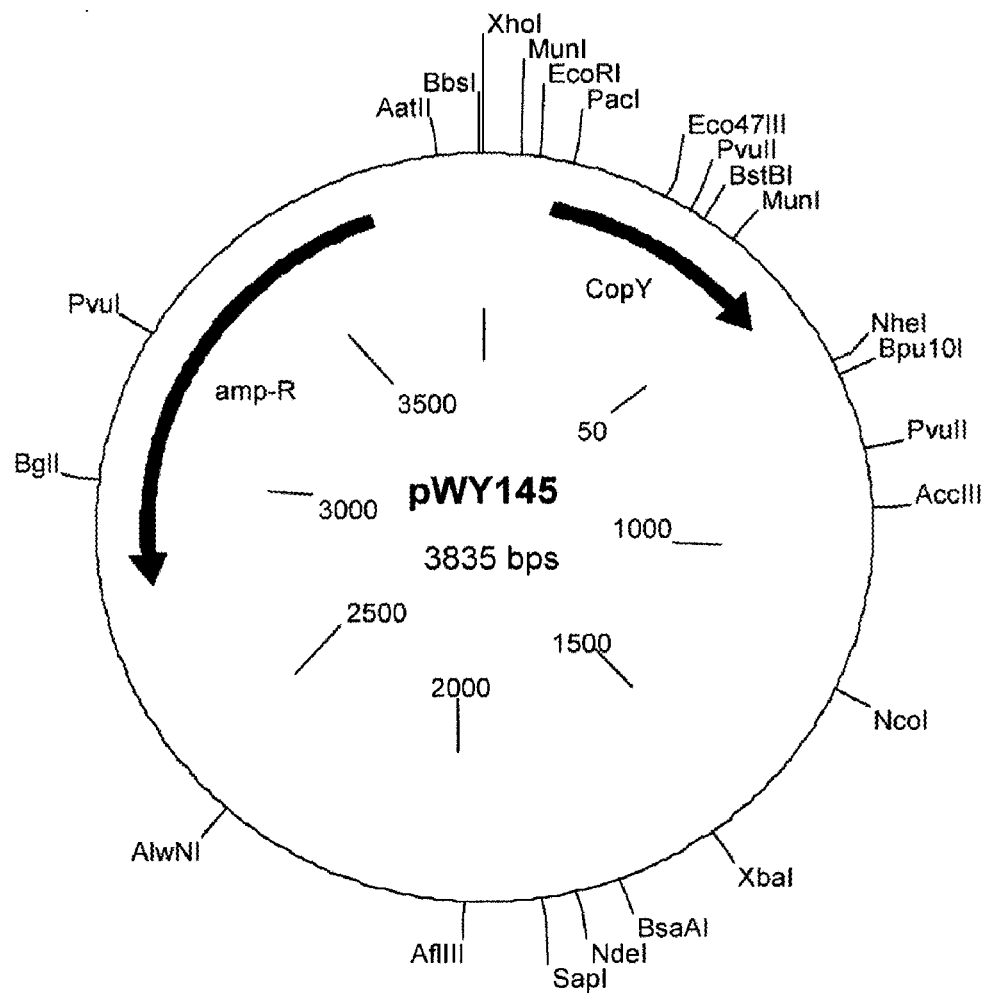
Figure 7. The pWY145 construct for the expression of 6xhis CopY

```
        NdeI
        ------
  1   CATATGCAG TATAAACTG ATTCTGAACGGC AAAACCCTG AAAGGCGAA ACCACCACCGAA

HisMetGln TyrLysLeu IleLeuAsnGly LysThrLeu LysGlyGlu ThrThrThrGlu
      |-------------------------GB1 sequence-------------------------

61   GCGGTGGAT GCGGCGACC GCGGAAAAAGTG TTTAAACAG TATGCGAAT GATAATGGCGTG

AlaValAsp AlaAlaThr AlaGluLysVal PheLysGln TyrAlaAsn AspAsnGlyVal
      -------------------------GB1 sequence-------------------------
                                                                MunI
                                                                ------
121   GATGGCGAA TGGACCTAT GATGATGCGACC AAAACCTTT ACCGTGACC GAAGCGCAATTG AspGlyGlu TrpThrTyr AspAspAlaThr LysThrPhe ThrValThr GluAlaGlnLeu
      -------------------------GB1 sequence-----------------| |-------
                    MunI
                    ------
181   ACCCAGGAA GATATTCAG CAGATTATGAAA CAATTGAAT AAAAAAGAA CCGGTGGAAACC ThrGlnGlu AspIleGln GlnIleMetLys GlnLeuAsn LysLysGlu ProValGluThr
      -------------------------Ymbs 38 sequence----------------------
                                                          BclI
                                                          --------
241   ATTGAATGC AACTGCATT CCGGGCCAGTGC GAATGCAAA AAACAGTAA TGATCA IleGluCys AsnCysIle ProGlyGlnCys GluCysLys LysGln--- ---Ser
      -----------------------Ymbs 38 sequence---------|STOP
```
(SEQ ID NO. 13)

Figure 8: The synthetic GB1-Ymbs38 gene

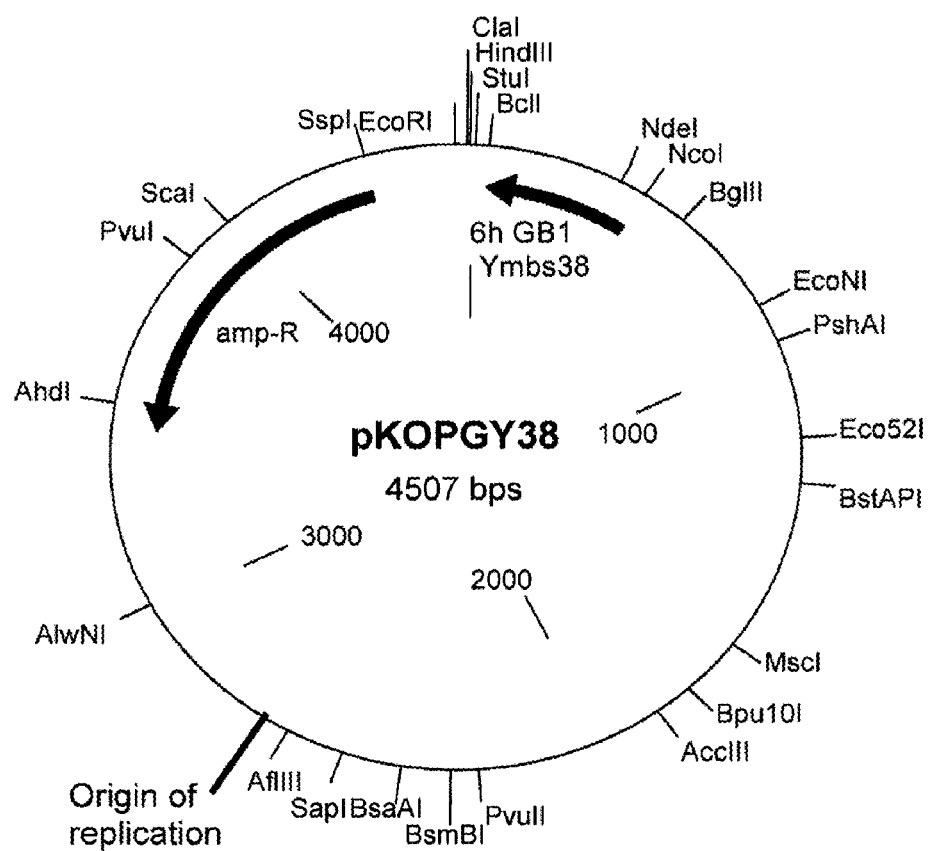
Figure 9. The plasmid construct for the expression of 6xhis GB1-Ymbs38

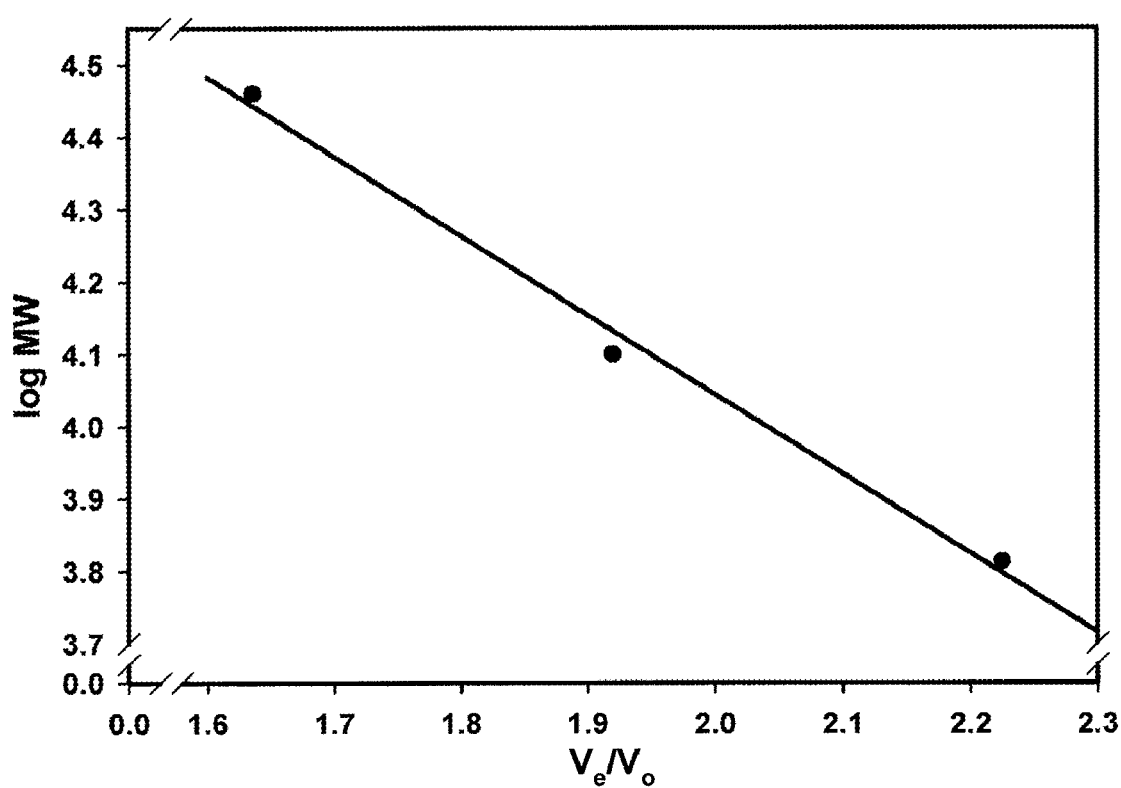
Figure 10. Molecular weight standard curve for the Shodex KW 803 HPLC column

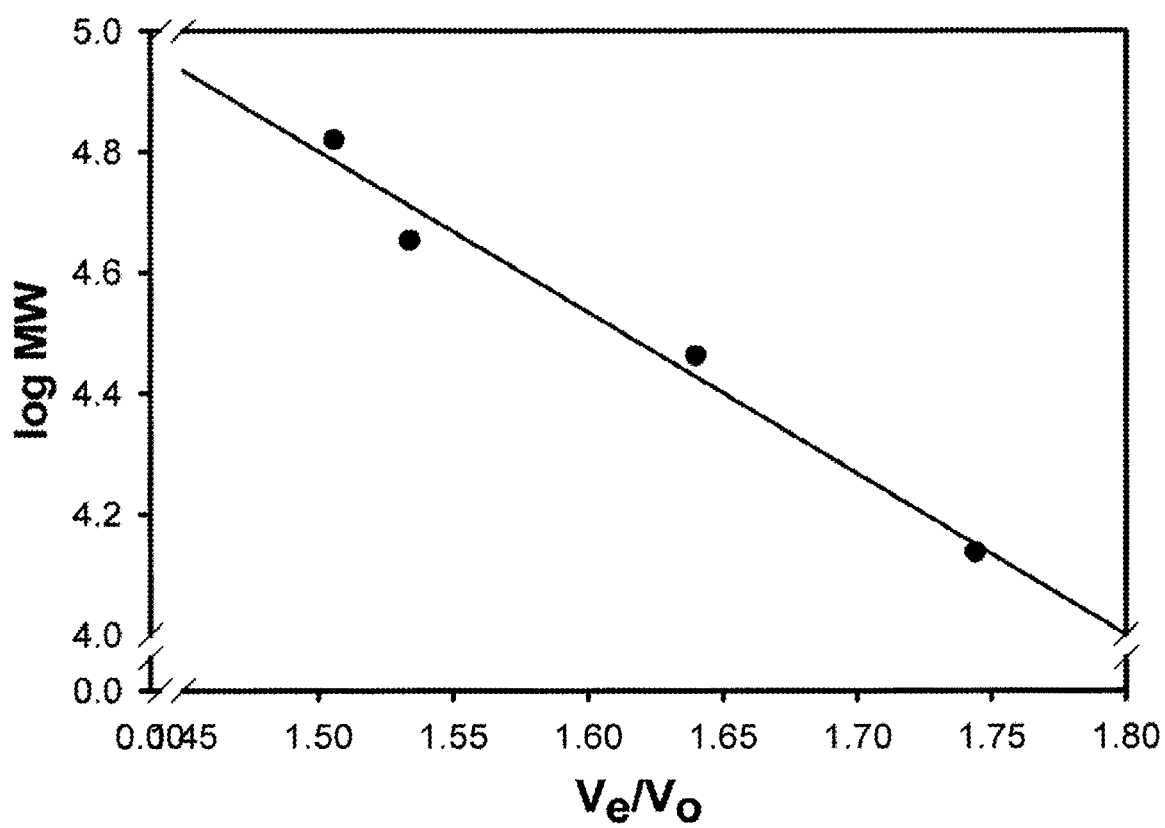
Figure 11. Molecular weight standard curve for the Shodex KW 803 HPLC column

| A1 | B | C | D | E | F |
|----|---|---|---|---|---|
| 2 | Zn(II)GY38, 6/9/06 | | | | |
| 3 | [loaded GY38] (M) | log [loaded | elution | weight average partition | observed fraction |
| 4 | | protein] (M) | volume (Ve) | coefficient ($\sigma$w) | of monomer |
| 5 | 0.000268 | =LOG(B5) | 11.15 | =(D5-6.8)/14.8 | =(E5-$E$19)/($E$21-$E$19) |
| 6 | 0.000128 | =LOG(B6) | 11.33 | =(D6-6.8)/14.8 | =(E6-$E$19)/($E$21-$E$19) |
| 7 | 0.0000604 | =LOG(B7) | 11.47 | =(D7-6.8)/14.8 | =(E7-$E$19)/($E$21-$E$19) |
| 8 | 0.0000301 | =LOG(B8) | 11.58 | =(D8-6.8)/14.8 | =(E8-$E$19)/($E$21-$E$19) |
| 9 | 0.0000142 | =LOG(B9) | 11.68 | =(D9-6.8)/14.8 | =(E9-$E$19)/($E$21-$E$19) |
| 10 | 0.00000682 | =LOG(B10) | 11.77 | =(D10-6.8)/14.8 | =(E10-$E$19)/($E$21-$E$19) |
| 11 | 0.00000349 | =LOG(B11) | 11.83 | =(D11-6.8)/14.8 | =(E11-$E$19)/($E$21-$E$19) |
| 12 | | | | | |
| 13 | | | | | |
| 14 | | | | | |
| 15 | | | | | |
| 16 | | | | | |
| 17 | | | | | |
| 18 | | | Ve of dimer | $\sigma$d of dimer | |
| 19 | | | 11.1 | =(D19-6.8)/14.8 | |
| 20 | | | Ve of monomer | $\sigma$m of monomer | |
| 21 | | | 12.03 | =(D21-6.8)/14.8 | |

| A1 | G | H | I |
|----|---|---|---|
| 2 | | | |
| 3 | calculated fraction | Equilibrium | (residual)^2 |
| 4 | of monomer | constant | |
| 5 | =(-1+(SQRT((1+(8*$H$5*B5)))))/(4*$H$5*B5) | 40187.194459 | =(F5-G5)^2 |
| 6 | =(-1+(SQRT((1+(8*$H$5*B6)))))/(4*$H$5*B6) | | =(F6-G6)^2 |
| 7 | =(-1+(SQRT((1+(8*$H$5*B7)))))/(4*$H$5*B7) | | =(F7-G7)^2 |
| 8 | =(-1+(SQRT((1+(8*$H$5*B8)))))/(4*$H$5*B8) | | =(F8-G8)^2 |
| 9 | =(-1+(SQRT((1+(8*$H$5*B9)))))/(4*$H$5*B9) | | =(F9-G9)^2 |
| 10 | =(-1+(SQRT((1+(8*$H$5*B10)))))/(4*$H$5*B10) | | =(F10-G10)^2 |
| 11 | =(-1+(SQRT((1+(8*$H$5*B11)))))/(4*$H$5*B11) | | =(F11-G11)^2 |
| 12 | | Sum of squares = | =SUM(I5:I11) |

| A1 | J | K | L |
|----|---|---|---|
| 2 | | | |
| 3 | | log [loaded | calculated $\sigma$w |
| 4 | | GY38] (M) | |
| 5 | | -3.5 | =$E$19+(-1+(SQRT(1+(8*$H$5*10^(K5)))))/(4*$H$5*10^(K5))*($E$21-$E$19) |
| 6 | | -4 | =$E$19+(-1+(SQRT(1+(8*$H$5*10^(K6)))))/(4*$H$5*10^(K6))*($E$21-$E$19) |
| 7 | | -4.5 | =$E$19+(-1+(SQRT(1+(8*$H$5*10^(K7)))))/(4*$H$5*10^(K7))*($E$21-$E$19) |
| 8 | | -5 | =$E$19+(-1+(SQRT(1+(8*$H$5*10^(K8)))))/(4*$H$5*10^(K8))*($E$21-$E$19) |
| 9 | | -5.5 | =$E$19+(-1+(SQRT(1+(8*$H$5*10^(K9)))))/(4*$H$5*10^(K9))*($E$21-$E$19) |

Figure 12. Excel Formula Spreadsheet for Large Zone Chromatograpy

| A1 | B | C | D | E | F |
|---|---|---|---|---|---|
| 2 | Zn(II)GY38, 6/9/06 | | | | |
| 3 | [loaded GY38] (M) | log [loaded protein] (M) | elution volume (Ve) | weight average partition coefficient ($\sigma$w) | observed fraction of monomer |
| 4 | | | | | |
| 5 | 2.68E-04 | -3.571865206 | 11.15 | 0.293918919 | 0.053763441 |
| 6 | 1.28E-04 | -3.89279003 | 11.33 | 0.306081081 | 0.247311828 |
| 7 | 6.04E-05 | -4.218963061 | 11.47 | 0.315540541 | 0.397849462 |
| 8 | 3.01E-05 | -4.521433504 | 11.58 | 0.322972973 | 0.516129032 |
| 9 | 1.42E-05 | -4.847711656 | 11.68 | 0.32972973 | 0.623655914 |
| 10 | 6.82E-06 | -5.166215625 | 11.77 | 0.335810811 | 0.720430108 |
| 11 | 3.49E-06 | -5.457174573 | 11.83 | 0.339864865 | 0.784946237 |
| 12 | | | | | |
| 13 | | | | | |
| 14 | | | | | |
| 15 | | | | | |
| 16 | | | | | |
| 17 | | | | | |
| 18 | | | Ve of dimer | $\sigma$d of dimer | |
| 19 | | | 11.1 | 0.290540541 | |
| 20 | | | Ve of monomer | $\sigma$m of monomer | |
| 21 | | | 12.03 | 0.353378378 | |

| A1 | G | H | I |
|---|---|---|---|
| 2 | | | |
| 3 | calculated fraction of monomer | Equilibrium constant | (residual)^2 |
| 4 | | | |
| 5 | 0.193498002 | 40187.19446 | 0.019525748 |
| 6 | 0.266935985 | | 0.000385108 |
| 7 | 0.362405623 | | 0.001256266 |
| 8 | 0.468649724 | | 0.002254285 |
| 9 | 0.595400865 | | 0.000798348 |
| 10 | 0.717671959 | | 7.60738E-06 |
| 11 | 0.814094349 | | 0.000849612 |
| 12 | | Sum of squares = | 0.025076973 |

| A1 | J | K | L |
|---|---|---|---|
| 2 | | | |
| 3 | | log [loaded GY38] (M) | calculated $\sigma$w |
| 4 | | | |
| 5 | | -3.5 | 0.301829675 |
| 6 | | -4 | 0.309138268 |
| 7 | | -4.5 | 0.319487044 |
| 8 | | -5 | 0.331704643 |
| 9 | | -5.5 | 0.342470639 |

Figure 13. Large Zone Calculations for Zn(II)GB1-Ymbs38

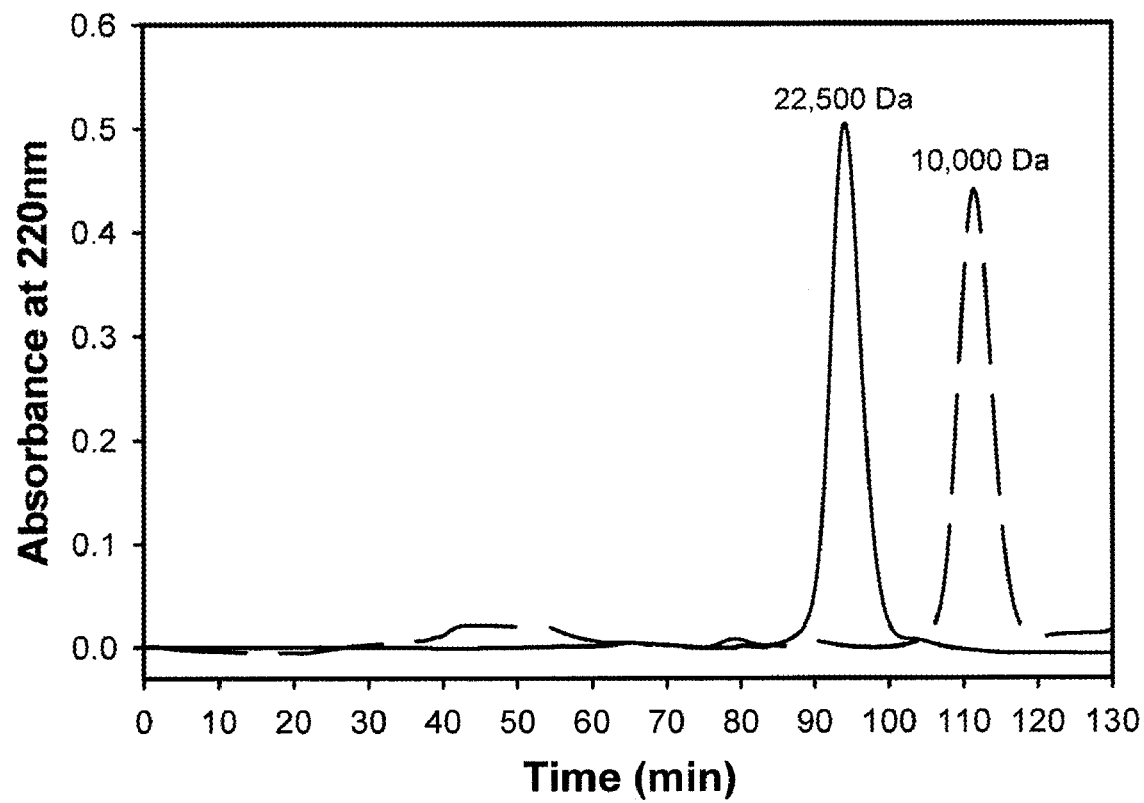
Figure 14. Gel Filtration Chromatography of GB1-Ymbs38

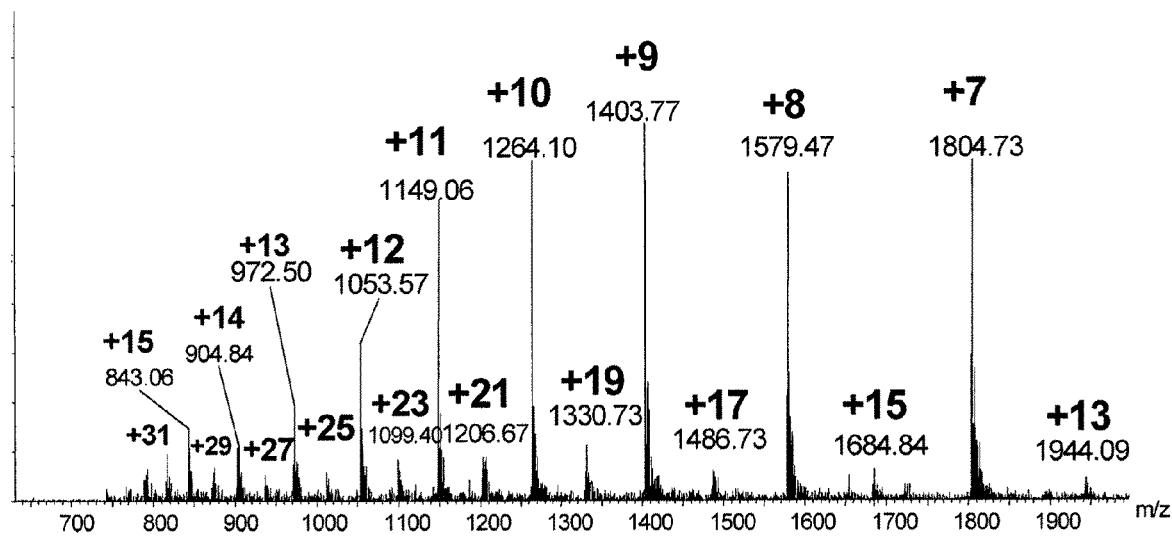
Figure 15. ESI mass spectrum of Zn(II)GB1-Ymbs38

1. The m/z values from the mass spectrum can be expressed as follows:

$$m/z = (MW + nH^+)/n$$

Where MW = the molecular mass of the sample, n = the integer number of charges on the ion, and H = the mass of a proton (1.008 Da).

2. Select two adjacent ions from the mass spectrum with the assumption that they differ by one charge.

$$1403.77 = (MW + nH^+)/n$$
$$1264.10 = (MW + (n+1)H^+)/(n+1)$$

3. Rearrange both equations to set them equal to MW, then set them equal to each other. Solve for n.

$$n(1403.77) - nH^+ = (n(1264.10) + 1264.10) - (nH^+ + H^+)$$
$$n(1403.77) - n(1264.10) = 1264.10 - H^+$$
$$n(139.67) = 1264.10 - H^+$$
$$n = 1263.10/139.67$$

$$n = 9.0$$

4. Insert the value for n back into the equation from Step 1 to solve for molecular mass.

$$1403.77 = (MW + (9*1.008))/9$$
$$(1403.77*9) - 9.072 = MW$$

$$MW = 12625 \text{ Da}$$

Figure 16. Method for calculating ion charge and molecular mass from the mass spectrum

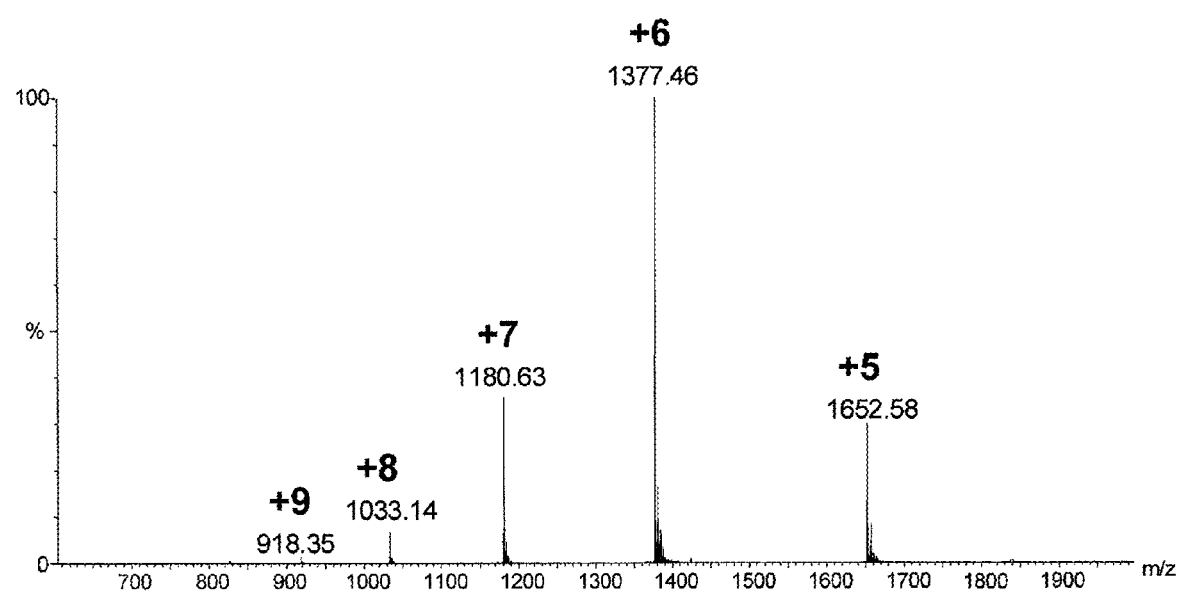
Figure 17. ESI mass spectrum of GB1.

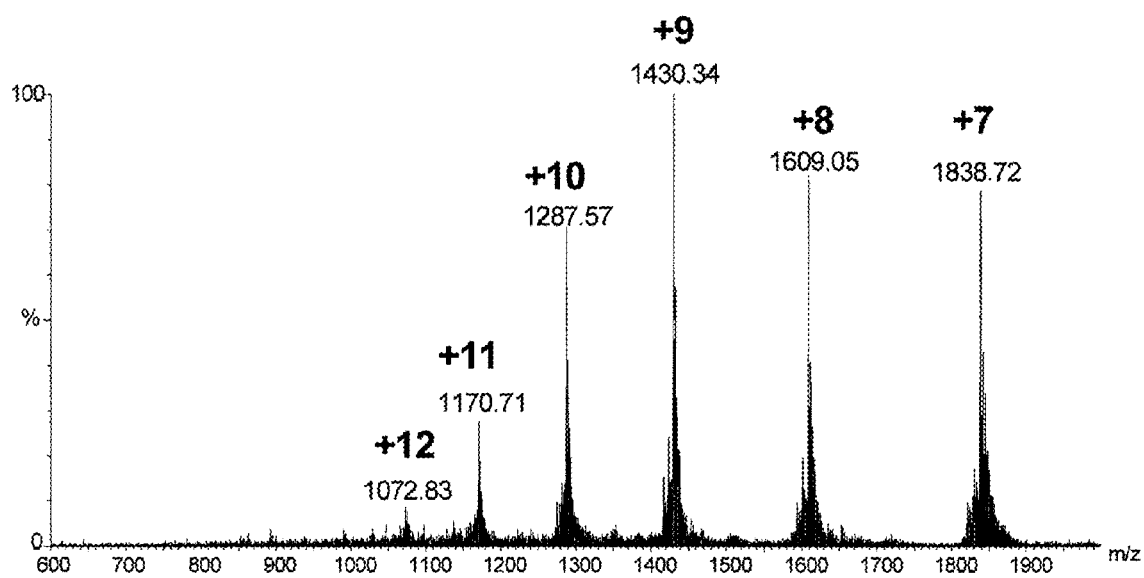
Figure 18. ESI mass spectrum of *apo*-GB1-Ymbs38

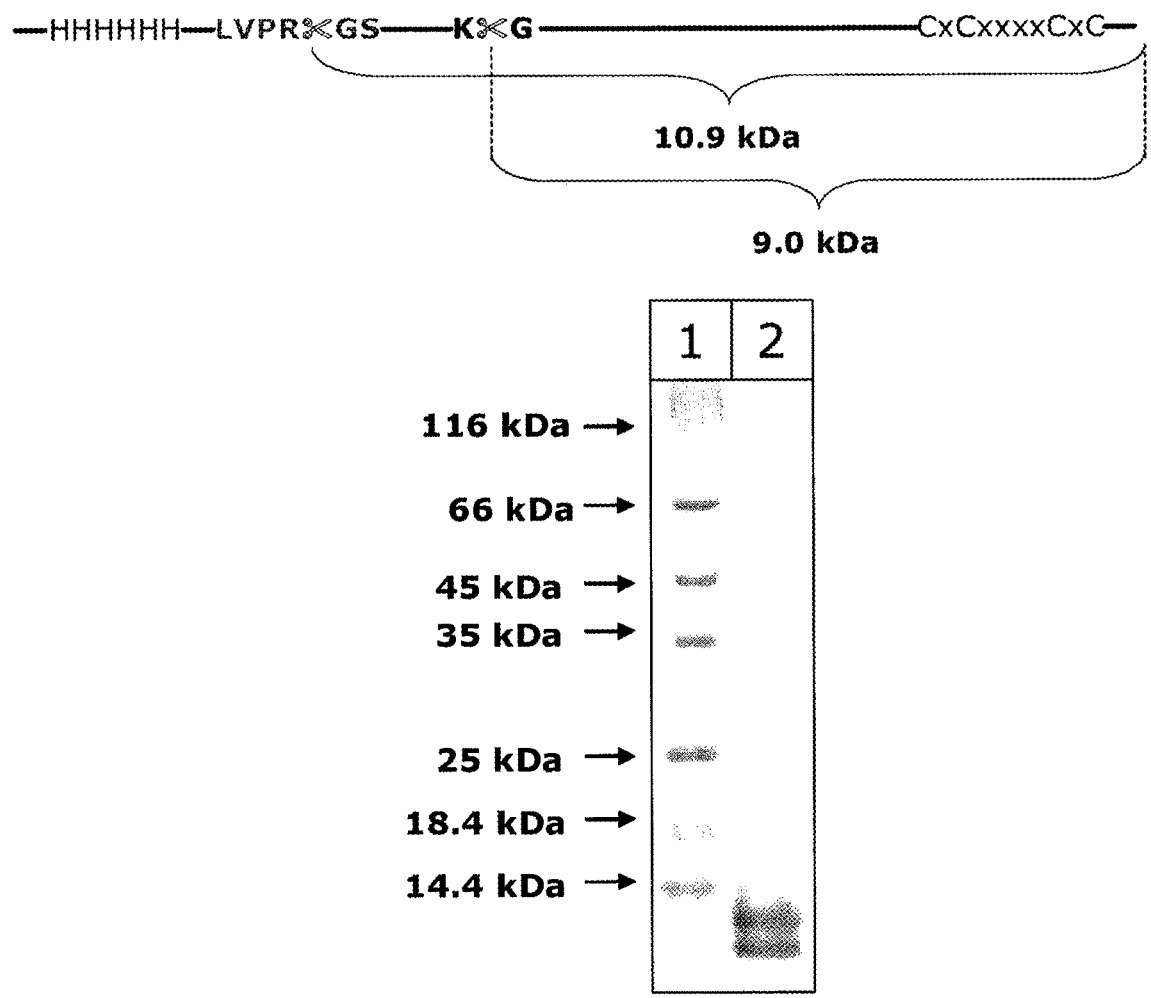
Figure 19. Thrombin cleavage of GB1-Ymbs38

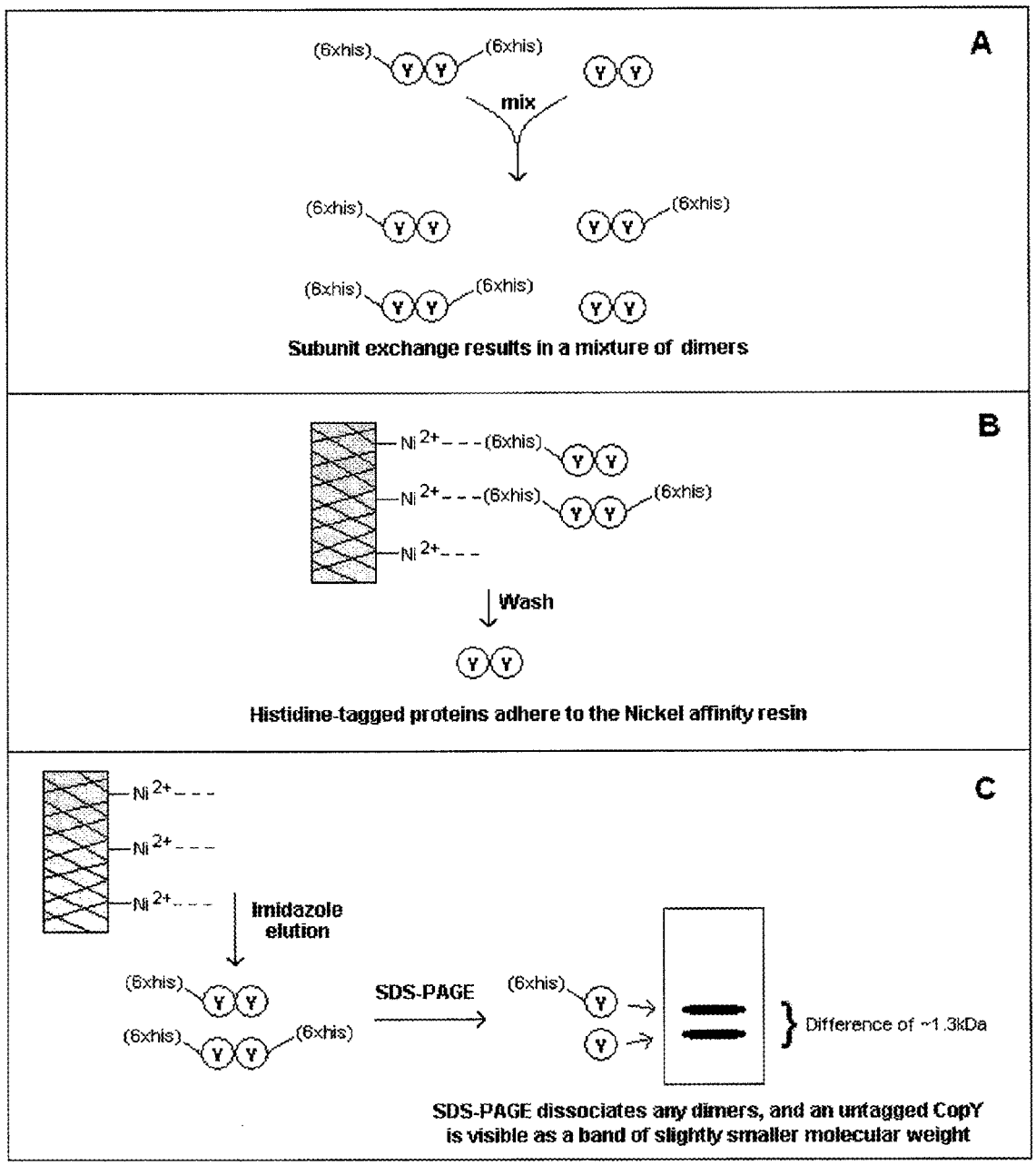
Figure 20. Schematic of HIS-Select Resin Binding Assay

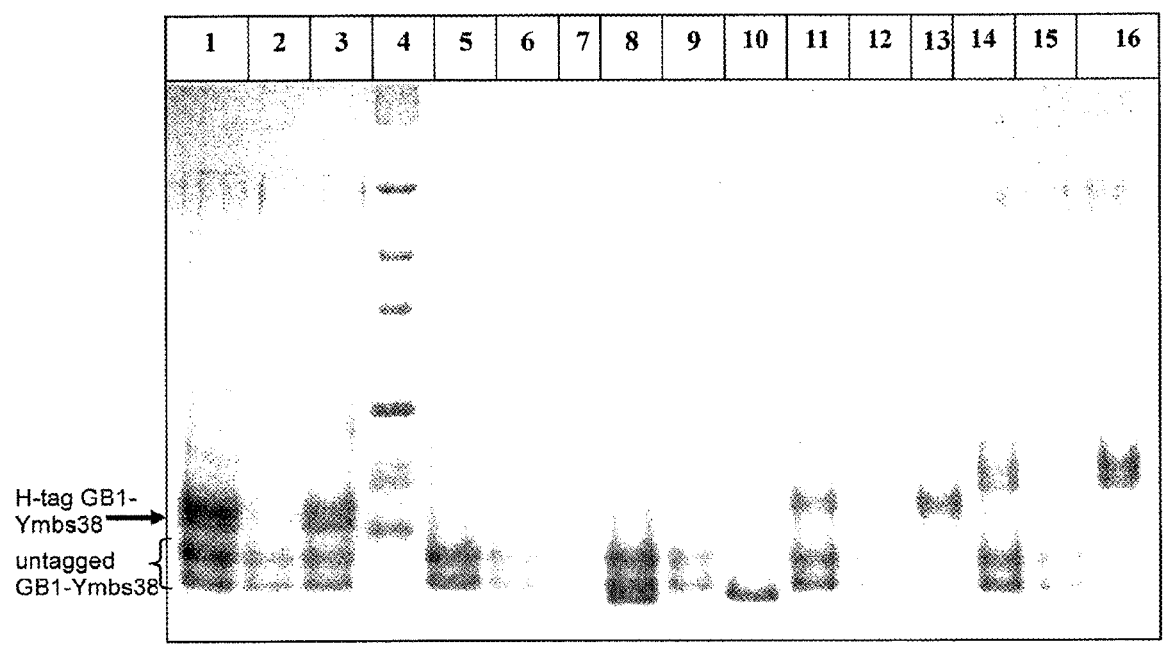
Figure 21. SDS-PAGE of HIS-Select Resin Binding Assay with GB1-Ymbs38 Variants

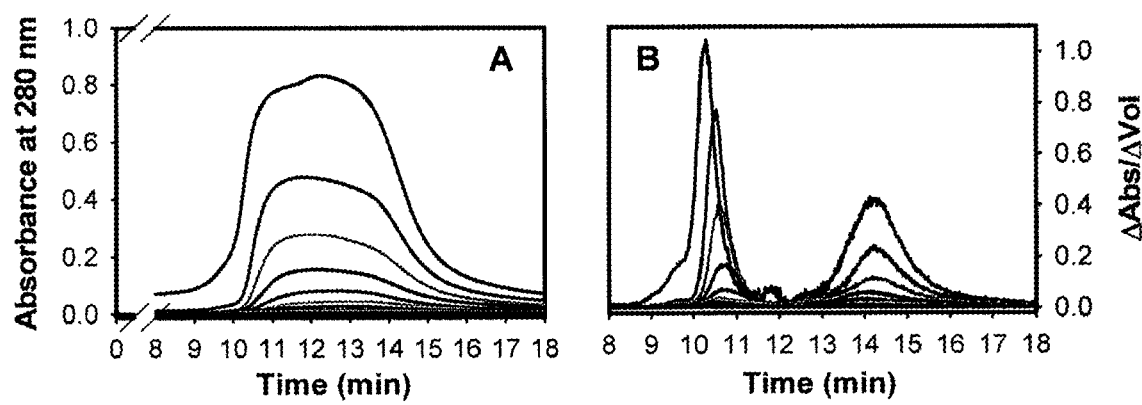
Figure 22. Large Zone Size Exclusion Chromatography on Zn(II)CopY

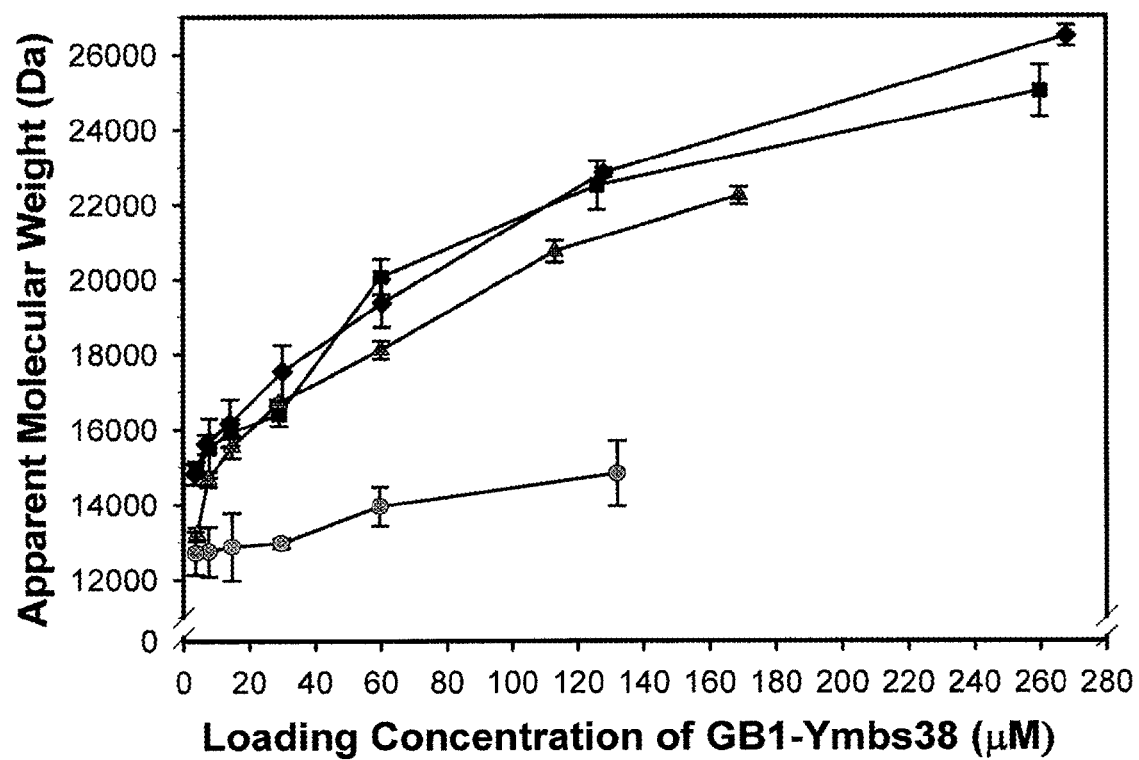
Figure 23. Comparison of Large Zone Chromatography Assays on GB1-Ymbs38

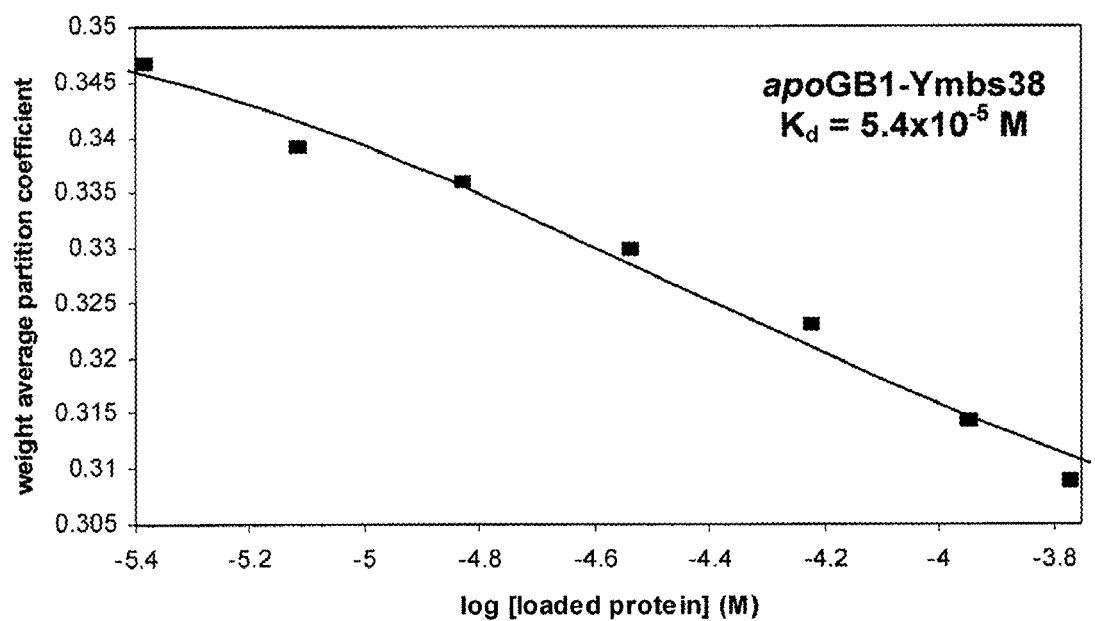
Figure 24. Non-linear Least Squares Best Fit of Large Zone Chromatography Data

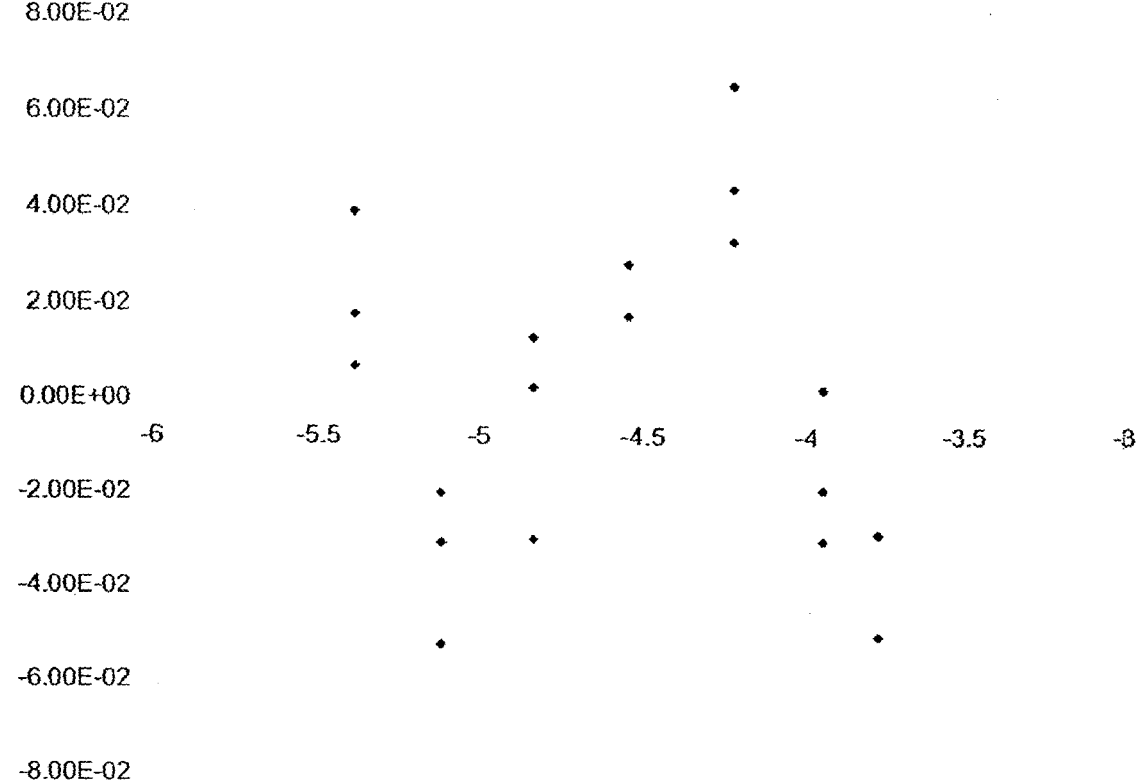
Figure 25. Residual plot of large zone chromatography data for *apo*-GB1-Ymbs38

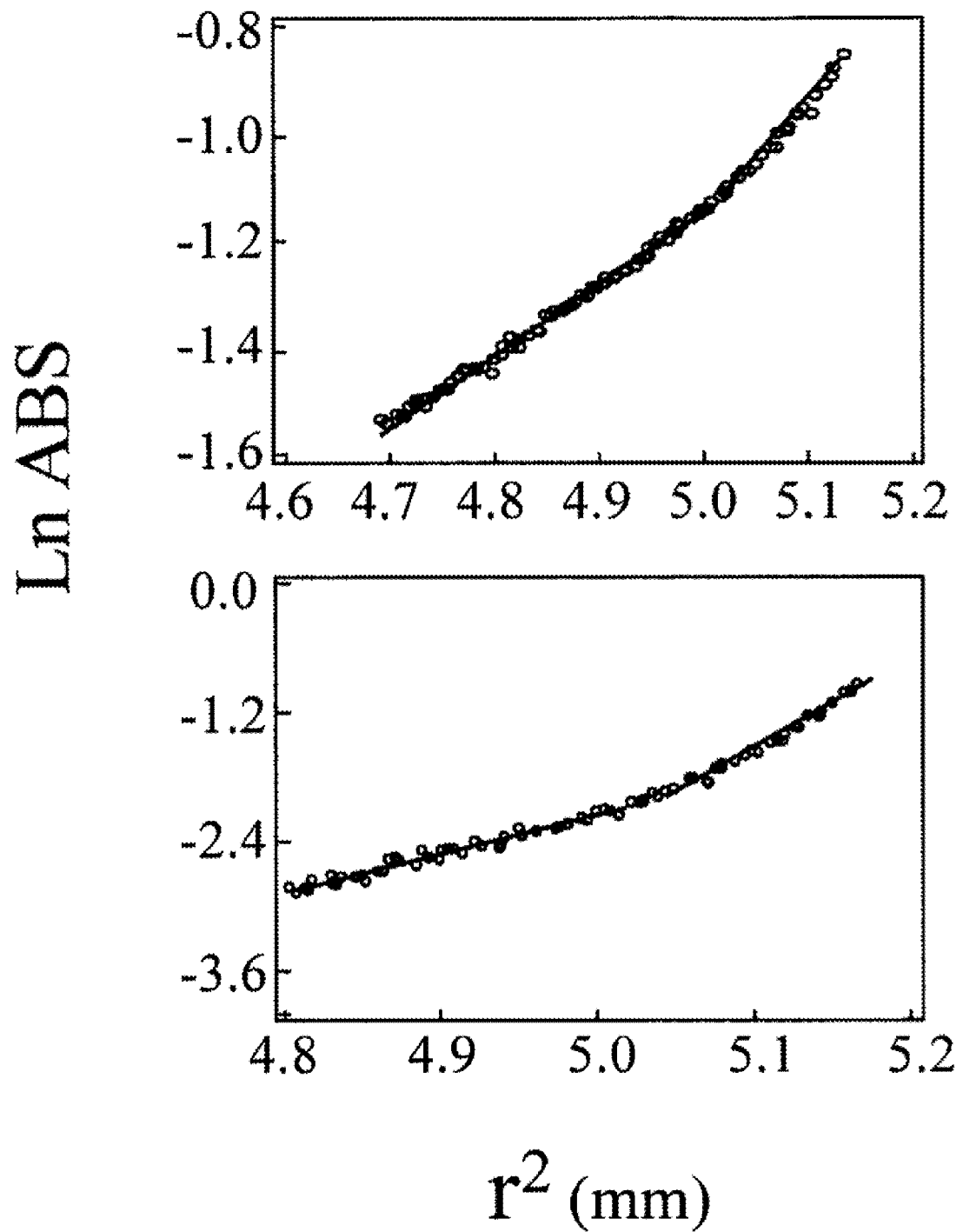
Figure 26. Analytical Ultracentrifugation

SELF-ASSEMBLED PROTEINS AND RELATED METHODS AND PROTEIN STRUCTURES

CROSS-REFERENCE TO RELATED APPLICATIONS

The present application is a divisional of U.S. patent application Ser. No. 11/805,188, filed May 22, 2007, entitled "Self-Assembled Proteins and Related Methods and Protein Structures," which is a continuation-in-part application of U.S. patent application Ser. No. 11/751,850, filed May 22, 2007, entitled "Self-Assembled Proteins and Related Methods," which claims priority to U.S. Provisional Patent Application Ser. No. 60/808,232, filed May 24, 2006, all of which are incorporated herein by reference.

BACKGROUND OF THE INVENTION

1. Field of the Invention

The present invention relates to protein self-assembly methods and, more particularly, to homo- and hetero-dimeric and multimeric assemblages of proteins and methods for their construction.

2. Description of the Prior Art

Understanding protein-protein interactions is critical to the understanding of how proteins participate in biological regulatory networks. All cellular signaling pathways rely on the joining or breaking of protein interactions to maintain correct function (Fry, D. C., Biopolymers, Peptide Science, 84:535-552, 2006) Protein-interactions have been defined to have different quaternary structures in which the simplest model is dimerization. In the search for new active agents, pharmaceutical companies are targeting therapeutic agents towards the interface of dimerization complexes (Tropsha, A. B. et al., PNAS USA, 88:9488-9492, 1991). In most cases, the goal is to disrupt protein-protein interactions at specific points within a biosignaling pathway (Graddis, T. J. M. et al., Biochemistry, 32:12664-12671, 1993). While knowledge on the subject is substantial and the pharmaceutical industry continues to develop drugs for inhibiting protein-interactions, there still is much to learn about how organisms organize the hundreds of interactions that take place at one time.

Dimerization is a critical structural feature of a myriad of proteins and the regulatory processes in which they participate. While the function of some proteins requires that they be in a dimeric form, the formation may not be directly involved in regulation. Dimerization is, however, involved in signal transduction pathways, repressor and transcription factor operations, enzyme activation and cell-to-cell communication. Dimer formation may occur prior to the signaling or regulatory event or the dimerization itself may be an integral part of the regulatory process.

At physiological concentrations, many dimers are in equilibrium with their monomer components. The dimers are bound together through an interface stabilized by a mixture of hydrophobic interactions, charge attractions and hydrogen bonds. Manipulation of the monomer-dimer equilibrium through ligand binding is a normal part of metabolism. Conformational changes induced by the binding of a ligand is a common way of promoting dimerization and, thereby, regulating the function of the proteins. The complexity of ligands ranges from simple ions to small signal molecules to complex proteins. Metalloregulation, the regulation of processes by the complexation of metal ions to proteins, is common in metal metabolic pathways and some oxidative stress responses. Generally, in metalloregulatory events the binding of metal ions to proteins is thought to induce or stabilize a conformational change in the structure to regulate its activity.

Conventional technology for creating dimers or multimers from proteins that normally are not coupled requires that the proteins be (1) chemically cross-linked, (2) created as direct gene fusions of the proteins involved or (3) indirectly linked by creating gene fusions with specific protein-protein binding motifs so that they, when translated, would be expected to specifically bind to each other through the added motifs with or without the aid of an exogenous regulatory ligand.

Generally, chemical cross-linking requires that the proteins be isolated and either (1) mixed together and treated with reagents to cause them to be covalently attached to each other or (2) each isolated protein be modified with different reagents that will enable the modified proteins to interact when mixed. In the former case, it is difficult to specifically dimerize the proteins into a single or limited series of structures because the crosslinks can form at multiple locations on the surfaces of the two proteins. In the latter case, each protein is modified separately with compounds that will couple with the other when mixed and thereby link the two proteins. Neither of these methods produces entirely specific quaternary structural links between the proteins. Both can lead to conformational changes in the proteins being modified and thus perturb their normal function and in some cases cause the complexes to be poorly soluble. Chemically cross-linked proteins are, however, commonly used in in vivo applications by first isolating the proteins, chemically cross-linking them and then injecting them into an organism. Chemical cross-links frequently are used to link enzymes to antibodies, which subsequently are used analytically in ELISA, tissue fixing or other in vitro analyses.

Chemical cross-linkers capable of diffusing across cell membranes have been used to study the state of oligomerization of dimeric and hexameric species and to probe for heterocomplexes. These studies are best performed on well characterized proteins so that appropriate linkers can be used. The weakness of these methods is that it is not possible to entirely limit the modification to only those proteins being targeted.

Though there are in vitro cleavable chemical cross-linkers, equilibrium between the monomer and dimer cannot be maintained, manipulated or used as a switch. Few of the modifying species can serve as a tool for subsequent affinity purification. Biotinylation, which has been an important tool for in vitro affinity purification (Pierce), cannot be used to purposely construct dimers or higher order species in vivo.

Pierce Biotechnology Inc. markets a wide range of chemical cross-linkers and bioconjugate linkers that interact with a variety of functional groups such as amino, sulphydryls and carboxylates. Some of these cross-linkers diffuse across membranes, but their reactions are largely non-specific and target a broad number of proteins within a cell.

Directly fusing two genes so that they are expressed as one fusion protein is commonly used to add an affinity tag to a protein. The affinity tag then enables the protein fusion to be purified more easily or, in some cases, used as an analytical tool to detect or measure the protein. Proteins, such as glutathione transferase (Pharmacia) and maltose binding protein (NEB); protein domains, such as S-tag (Novagen) and FLAG (Kodak); and 6 histidine repeats (SEQ ID NO: 37) (His tag) frequently are used for affinity purification purposes. Genes or gene fragments also are used to target the fusion protein to specific cellular locations. Novagen (and others) markets a vector that produces a gene fusion of the protein of interest to an export sequence so that the nascent protein will be excreted into the periplasmic space.

The S-tag, FLAG and, especially, the His tag are not as prone to cause folding problems in their fusion partners. However, it is relatively common for the resultant large glutathione transferase and maltose binding protein fusions to have solubility and expression problems. The His tag, which is the most commonly used affinity purification tag on the market today, it the most advantageous affinity tag because it works through a coordination complex and can be used in denaturing conditions. However, although very useful for affinity methods, all of these methods do not enable the construction of homodimers or specific heterospecies.

The direct fusion of the domains derived from the FKDP protein to the proteins of interest can be used to produce homodimers (ARIAD Pharmaceuticals, Inc.) under the control of exogenous rapamycin or related compounds due to the FKDP protein's high affinity for rapamycin. Two FKDP domains bind to each molecule (ligand) or rapamycin. Similarly, using hetero-fusions to FKDP and FRB, domain-specific heterodimers can be induced to form through the addition of a modified rapamycin (ARIAD Pharmaceuticals, Inc.). The regulated feature of these systems is useful and has been used in trafficking studies and may find uses in drug delivery systems. The size and complexity of the fusion proteins, however, pose problems in some cases. The delivery of rapamycin to the cell, tissue or organisms can be difficult. As designed, the monomer to dimer affinity cannot be modified.

There are several cloning systems, so called two-hybrid systems, where the possibility of protein-protein interactions between heteromers can be probed through the formation of dimeric species (Invitrogen and others). The two-hybrid systems also can be used to explore the interactions between specific dimers.

While these systems excel at probing for interactions between one protein and a library of others, they do not enable the formation of homo-dimers of a protein or hetero-dimer formation between proteins selected by the user. The system is, by its nature, linked to a reporter system. In addition, the two-hybrid systems cannot be used to build higher order species, establish an equlibria between the monomer and dimer, etc., or be regulated and used in trafficking studies.

The fusion of genes to a gene or gene fragment, as proposed for the hook motif, enables the formation of homo-dimers in vivo. The possibility of producing fusions of this type has been explored through manipulation of classical leucine-zippers and zinc-fingers. Both of these motifs require a larger sequence be attached to the desired proteins. Both the zipper and finger motifs cannot have their monomer-dimer equilibrium easily manipulated, be used as a switch, be used readily in affinity purification strategies or be used easily to make discrete multimer complexes. To the best of the inventor's knowledge, neither the leucine-zipper nor the zinc finger motifs has been utilized in commercial applications, although the leucine-zipper motif has been explored by an industry group.

With respect to the direct purification of fusion proteins by affinity methods, there are many choices. His-tag (Pharmacia, Sigma and others), S-tag (Novagen), FLAG (Kodak), GST-tag (Pharmacia and others) and maltose binding protein tags all are used in gene fusion based systems to aid in the purification of bacterial and yeast over-expression systems, but these systems are not used in vivo or in vitro to construct dimer or higher order structures and for the most part they are not suited to that task.

There exists a need, therefore, for sequence ("hook") motifs useful as linkers as well as for a method to link proteins to form specific hetero- and homo-dimeric and multimeric protein structures in the living body in vivo and in a test tube or apparatus in vitro.

SUMMARY OF THE INVENTION

It is an object of the present invention to provide gene sequences for forming homo-dimers, hetero-dimers and multimers of proteins in vivo and in vitro.

It is another object of this invention to provide a method of linking proteins without conformational changes in the proteins.

It is a further object of this invention to provide a method of linking proteins that enables the construction of homodimers of proteins or construction of heterodimers between proteins.

It is another object of the present invention to provide protein structures produced by the methods of the present invention.

The above needs are met and objects accomplished by providing a peptide sequence, said peptide sequence comprising at least one component comprised of a $CxCx_{(4-6)}CxC$ (SEQ ID NO: 1)-metal binding loop, wherein the peptide sequence produces peptides or proteins. The $CxCx_{(4-6)}CxC$ (SEQ ID NO: 1)-metal binding loop can be attached to aliphatic repeat groups, which increases the stability of the component. An example of a $CxCx_{(4-6)}CxC$ (SEQ ID NO: 1)-metal binding loop is, without limitation, CxCxxxxCxC (SEQ ID NO: 38). The peptides or proteins produced therefrom form homo-dimers, hetero-dimers and multimers of proteins both in vivo and in vitro. The peptide sequence comprising at least one component comprised of a $CxCx_{(4-6)}CxC$ (SEQ ID NO: 1)-metal binding loop and aliphatic repeat groups can include, for example, the following sequence:

```
                                            (SEQ ID NO: 2)
ATLTQEDIQQIMKQLNKKEPVETIECNCIPGQCECKKQ
```

The present invention also provides a genetic sequence that transcribes the peptide sequence comprised of the $CxCx_{(4-6)}CxC$ (SEQ ID NO: 1)-metal binding loop and aliphatic repeat groups.

The present invention further provides a method of constructing assemblages of proteins with linking between the proteins. The method is comprised of forming a hydrophilic sequence ("hook") motif, comprised of a metal binding loop sequence attached to at least one aliphatic repeat sequence; providing a plurality of proteins; and mixing the plurality of proteins so that they self-assemble in the presence of the metal binding loop in order to form protein structures, such as, without limitation, homo-dimers, hetero-dimers or multimers.

The attachment of the metal binding loop sequence to the at least one aliphatic repeat sequence allows for the formation of specific interactions of the plurality of proteins. The aliphatic repeat sequence contains residues which contribute to the stability and specific interaction of the plurality of proteins.

The metal of the metal binding loop is, for example and without limitation, zinc [Zn(II)] or copper [Cu(I)].

The homo-dimers, hetero-dimers and multimers are effective for both in vivo and in vitro uses.

The present invention still further provides protein structures produced by the methods of the present invention, in which the protein structures are characterized as being suitable for use for, without limitation, diagnostic reagents; biomarkers; metal-activated switches; cell-trafficking studies; affinity purification of in vivo constructs; nanoscale construction; for imaging of cells and tissues such as, without limitation, visible imaging, fluorescent imaging and confocal imaging; delivery of proteins or pharmaceuticals having said proteins bound thereto to specific tissues or cells; purifying and separating compounds; cell research; and discovery of compounds for treating disease.

BRIEF DESCRIPTION OF THE DRAWINGS

The Patent or Application File contains at least one drawing executed in color. Copies of this patent or patent application publication with color drawing(s) will be provided by the office upon request and payment of the necessary fee.

A full understanding of the invention can be gained from the following description of the preferred embodiments when read in conjunction with the accompanying drawings in which:

FIG. 2 shows realized and potential hook motifs (SEQ ID NOS: 2-12, respectively, in order or appearance) according to embodiments of the present invention;

FIG. 6 shows a pWH6 construct for the expression of 6× his (SEQ ID NO: 37) CopY;

FIG. 7 shows a pWY145 construct for the expression of 6× his (SEQ ID NO: 37) CopY;

FIG. 8 shows a sequence of a synthetic gene (SEQ ID NO: 13), as well as the translated fusion protein sequence (SEQ ID NO: 40), according to embodiments of the present invention;

FIG. 9 shows a plasmid construct for the expression of 6× his (SEQ ID NO: 37) GB1-Ymbs38;

FIG. 10 shows a first molecular weight standard curve for a Shodex KW 803 HPLC column;

FIG. 11 shows a second molecular weight standard curve for a Shodex KW 803 HPLC column;

FIG. 12 shows an excel formula spreadsheet for large zone chromatography;

FIG. 13 shows large zone calculations for Zn(II) GB1-Ymbs38;

FIG. 14 shows gel filtration chromatography of GB1-Ymbs38;

FIG. 15 shows ESI mass spectrum of Zn(II) GB1-Ymbs38;

FIG. 16 shows a method for calculating ion charge and molecular mass from the mass spectrum;

FIG. 17 shows ESI mass spectrum of GB1;

FIG. 18 shows ESI mass spectrum of apo-GB1-Ymbs38;

FIG. 19 shows thrombin cleavage of GB1-Ymbs38 (SEQ ID NOS: 37, 39 and 38, respectively, in order of appearance);

FIG. 20 shows a schematic of HIS-Select Resin Binding Assay. (A) shows a 6× histidinte tagged (6× his) (SEQ ID NO: 37) version of the protein mixed with an untagged protein; (B) shows the protein mixture applied to the HIS-Select affinity resin; 6× His tag disclosed as SEQ ID NO: 37; and (C) shows imidazole added to elute the histidine-tagged (SEQ ID NO: 37) protein from the resin;

FIG. 21 shows SDS-PAGE of HIS-Select Resin Binding Assay with GB1-Ymbs38 Variants;

FIG. 22 shows large zone size exclusion chromatography on Zn(II) CopY. (A) is a chromatograph showing the 280 nm absorbance trace for the large zone experiment; and (B) shows the first derivative cureves of the elution profiles from (A);

FIG. 23 shows a comparison of large zone chromatography assays on GB1-Ymbs38;

FIG. 24 shows non-linear least squares best fit of large zone chromatography data;

FIG. 25 shows a residual plot of large zone chromatography data for apo-GB1-Ymbs38; and FIG. 26 shows analytical ultracentrifugation data to confirm size exclusion data. (A) shows a 85%-15% Zn(II) CopY dimer-monomer mixture and (B) shows a 25%-75% an apo-CopY dimer-monomer mixture without Zn(II);

DESCRIPTION OF THE PREFERRED EMBODIMENTS

Figure 1:
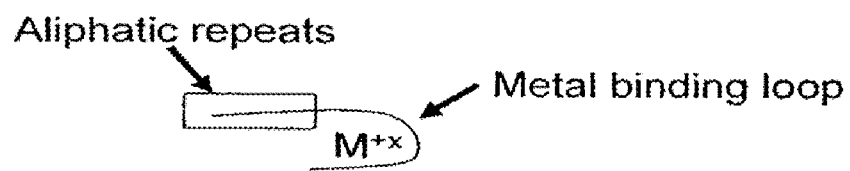
FIG. 1 shows the hook motif according to e embodiments of the present invention.

The present invention provides homo- and -hetero-dimeric and multimeric self-assembly of proteins and methods for their construction.

In an embodiment of the present invention, there is provided a peptide sequence, said peptide sequence comprising at least one component comprised of a $CxCx_{(4-6)}CxC$ (SEQ ID NO: 1)-metal binding loop, wherein the peptide sequence produces peptides or proteins. The $CxCx_{(4-6)}CxC$ (SEQ ID NO: 1)-metal binding loop can be attached to aliphatic repeat groups, which increases the stability of the component. An example of a $CxCx_{(4-6)}CxC$ (SEQ ID NO: 1)-metal binding loop is, without limitation, CxCxxxxCxC (SEQ ID NO: 38). The peptides or proteins produced therefrom form homo-dimers, hetero-dimers and multimers of proteins both in vivo and in vitro. The peptide sequence comprising at least one component comprised of a $CxCx_{(4-6)}CxC$ (SEQ ID NO: 1)-metal binding loop and aliphatic repeat groups can include, for example, the following sequence:

(SEQ ID NO: 2)
ATLTQEDIQQIMKQLNKKEPVETIECNCIPGQCECKKQ

In another embodiment of the present invention, there is provided a genetic sequence that transcribes the peptide sequence comprised of the $CxCx_{(4-6)}CxC$ (SEQ ID NO: 1)-metal binding loop and aliphatic repeat groups.

In a further embodiment of the present invention, there is provided a method of constructing assemblages of proteins with linking between the proteins. The method is comprised of forming a hydrophilic sequence ("hook") motif, comprised of a $CxCx_{(4-6)}CxC$ (SEQ ID NO: 1)-metal binding loop sequence, which can attach to at least one aliphatic repeat sequence; providing a plurality of proteins; and mixing the plurality of proteins so that they self-assemble in the presence of the metal binding loop in order to form protein structures, such as, without limitation, homo-dimers, hetero-dimers or multimers.

A non-limiting example of the $CxCx_{(4-6)}CxC$ (SEQ ID NO: 1)-metal binding loop sequence is CxCxxxxCxC (SEQ ID NO: 38).

The attachment of the metal binding loop sequence to the at least one aliphatic repeat sequence allows for the formation of specific interactions of the plurality of proteins. The aliphatic repeat sequence contains residues which contribute to the stability and specific interaction of the plurality of proteins.

The metal of the metal binding loop is, for example and without limitation, zinc [Zn(II)] or copper [Cu(I)].

The homo-dimers, hetero-dimers and multimers are effective for both in vivo and in vitro uses.

In still a further embodiment of the present invention, there is provided protein structures produced by the methods of the present invention, in which the protein structures are characterized as being suitable for use for, without limitation, diagnostic reagents; biomarkers; metal-activated switches; cell-trafficking studies; affinity purification of in vivo constructs; nanoscale construction; for imaging of cells and tissues such as, without limitation, visible imaging, fluorescent imaging and confocal imaging; delivery of proteins or pharmaceuticals having said proteins bound thereto to specific tissues or cells; purifying and separating compounds; cell research; and discovery of compounds for treating disease.

Suitable aliphatic repeat sequences may be, without limitation, hydrophobic amino acids such as valine, isoleucine, proline, alanine, methionine, tyrosine, phenylalanine or synthetic residues having similar hydrophobic properties. The aliphatic repeat sequences may repeat in the peptide sequence, for example and without limitation, about every four amino acid residues.

Hook motifs are shown in FIG. 2. Residues around cysteines are responsible for the specificity of the interactions. The top sequence in FIG. 2 has been fully tested and the highlighted portion shows hydrophobic residues, frequently as aliphatic repeats. The cysteines in the metal binding motif are in bold. Four of the genes containing these sequences have been cloned.

The aliphatic repeats support dimerization even in the absence of the metal binding loop, constituting the bulk of the stabilization. However, in the absence of a metal binding loop, there is a higher probability of forming non-specific interactions and non-specific hetero-dimers and multimers. The residues around the aliphatic repeats also contribute to the specificity. Both parts of the peptide sequence are involved in the specificity and stabilization of the protein-protein interactions. To construct dimers or multimers, the DNA sequence that codes for the peptides must be fused to the gene or genes of interest at one of the two termini or, possibly, between two domains. Homo-dimers are formed by fusing a single DNA sequence coding for a peptide motif to the gene of interest. The resultant protein will self assemble into a specific dimer in the presence of zinc(II) or copper(I). Formation of specific hetero species requires that two different motifs, which have a higher affinity for each other than for themselves, be used with the genes of interest. In the absence of metal ions, the motif is prone to more non-specific interactions with similar aliphatic motifs to make dimers or multimers. Most cells maintain an intracellular zinc concentration more than sufficient to insure that zinc is bound to the sequence. FIG. 2 shows only a partial selection of the sequences that can be used for these operations according to the embodiments of the present invention.

The advantageous features provided by the metal binding peptides (i.e., the "sequence motif" or "hook motif") of the present invention are: (1) the sequences are short, and thus they are less likely to interfere with the folding of their fusion partners; (2) the sequences are hydrophilic, and thus they aid, not decrease, the solubility of the fusions; (3) the sequences can be used to form dimers and/or multimers for in vivo and in vitro applications; (4) it is possible to select a range of dissociation constants by varying the length of the aliphatic repeat region; (5) it is possible to build a metal-activated dimer (i.e., metal ions are easily administered); (6) due to the variety of sequences available, a large number of distinct constructs can be produced; (7) the sequences can be used as an affinity tag with similarly tagged proteins, in which the tag then can be used to purify or detect fusion proteins.

The most advantageous feature of the hook motif is the ability to use it to form specific user-directed self-assembling hetero-dimers in vivo. In natural settings, the motif aids in or supports dimerization. The hook motif is found at the termini of proteins and in separate regions or domains of proteins and can, in principle, be utilized in similar positions when used to make novel dimers.

Specific dimerization or the formation of higher order structures is difficult in that it requires the use of large scale structures to interface with one another. One benefit of the sequence motif of the present invention is that it is small and hydrophilic and, therefore, is less likely to interfere with the structural fold and function of the proteins being dimerized. In this case, the dimerization motif is small and the interaction is weakened by the removal of the metal ion. The opportunity to use this feature in living cells or in the construction of nanoscale fabrications outside of cells is unique. The potential to use the metal-binding-dimerization motif in the direct purification of the fusion proteins also is a significant benefit.

Figure 3:
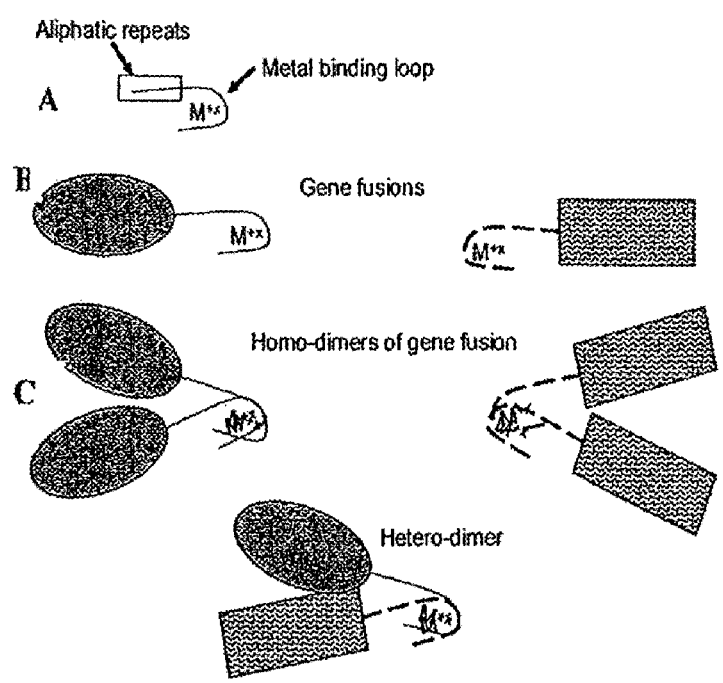
FIG. 3 shows the hook motif according to embodiments of the present invention, in which (A) contains a CxCxxxxCxC (SEQ ID NO: 38) motif and an aliphatic repeat; (B) shows fusion proteins constructed to express the motif; and (C) shows proteins expressing the motif and connecting to make dimers.
Figure 4:
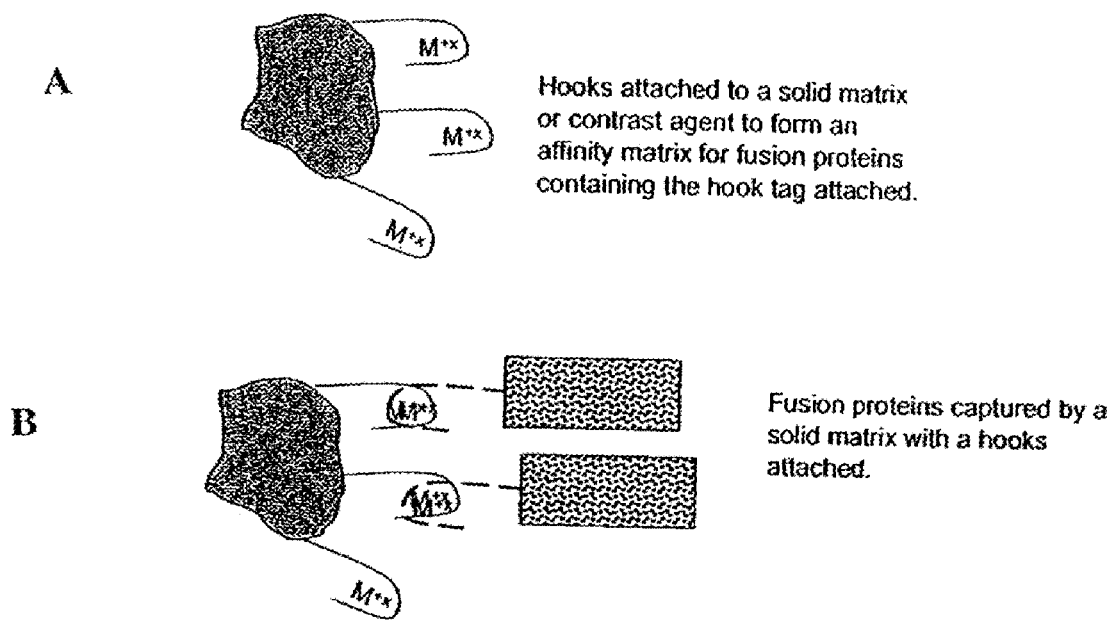
FIG. 4 shows hook motifs attached to solid resins for capturing proteins expressing the motifs according to embodiments of the present invention.
Figure 5:
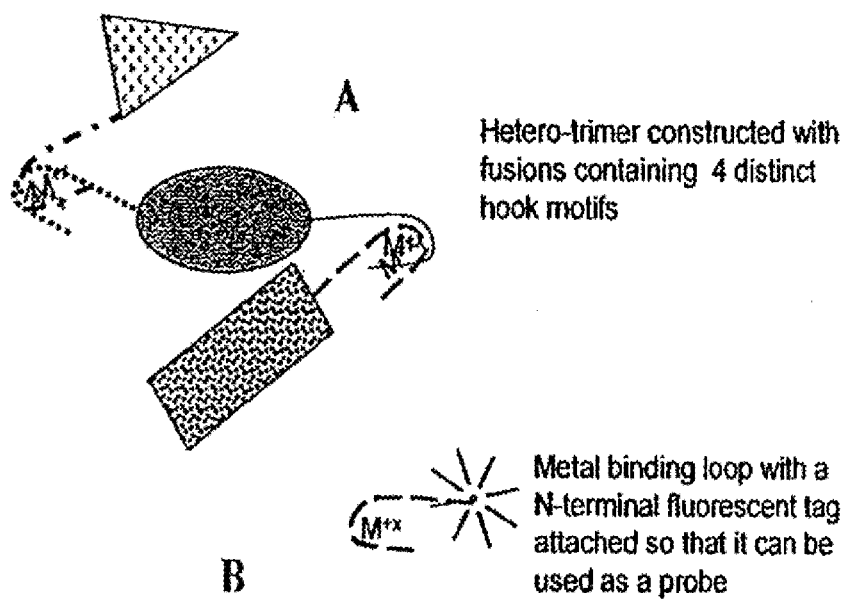
FIG. 5 shows motifs with varying affinities, in which (A) shows a hetero-trimer constructed with fusions containing four distinct hook motifs; and (B) shows a metal binding loop with an attached N-terminal fluorescent tag used as a probe.

Various ways that the hook motif of the present invention can be employed are shown in FIGS. 3, 4 and 5.

In FIG. 3A, the hook motif is shown to contain a CxCxxxx-CxC (SEQ ID NO: 38) motif and an aliphatic repeat. FIG. 3B shows fusion proteins constructed to express the motif FIG. 3C shows proteins expressing the motif and connecting to make dimers. Any proteins expressing the hook motif can participate in the dimer interaction.

Hook motifs attached to solid resins can be utilized to capture proteins expressing the hook motifs. For example, in FIG. 4A, hooks are attached to a solid matrix or contrast agent to form an affinity matrix for fusion proteins containing the hook tag attached. In FIG. 4B, fusion proteins are captured by a solid matrix with hooks attached.

FIG. 5A shows a hetero-trimer fused protein constructed with fusions containing four distinct hook motifs. Thus, the construction of motifs with varying affinities enables specific higher order structures to be built. FIG. 5B shows a metal binding loop with an N-terminal fluorescent tag attached so that it can be used as a probe. In this way, dye molecules attached to a motif can bind to other molecules that contain the hook motif for labeling, cellular trafficking or delivery studies.

There are 48,218 known peptide sequences in the human genome. Of these, peptide sequences, 175 have the sequence motif of the present invention. Many of these peptide sequences are different splice variants of the same gene. Thus, there are approximately eighty-five unique human genes that have the sequence motif of the present invention. A blast analysis demonstrates that slightly less than half of the genes, i.e., thirty-seven genes, do not share significant homology to other genes with the sequence motif. The gene families contain between two and nine genes. The biggest family is the metallothioneins, followed by the heparan-sulfate 6-O sulfotransferases. In the mouse genome, there are eighty-six unique genes with the sequence motif of the present invention. Table 1 provides a non-limiting example of eighty-five human genes which may contain the sequence motif for the $CxCx_{(4-6)}CxC$ (SEQ ID NO: 1)-metal binding loop and aliphatic repeat groups of the present invention, including their names and description.

TABLE 1

Human Genes Containing Sequence Motif for CxCxxxxCxC-Metal (SEQ ID NO: 38) Binding Loop and Aliphatic Repeat Groups

| EnsemblPeptide_ID | ID | Gene | Description |
|---|---|---|---|
| ENSP00000234487 | CLCN6_HUMAN | CLCN6 | Chloride channel protein 6 (ClC-6)xxxxx |
| ENSP00000354348 | Q8N962_HUMAN | | CDNA FLJ38312 fis, clone FCBBF3021506 |
| ENSP00000247992 | Q5R387_HUMAN | | Novel protein, lipase A2 family |
| ENSP00000344207 | 728969 | | predicted protein, similar to HS6ST1 (heparan-sulfate 6-O-sulfotransferase) |
| ENSP00000363889 | Q5T3S7_HUMAN | RAP1 | GTPase activating protein 1 |
| ENSP00000354614 | Q9UI23_HUMAN | | |
| ENSP00000330393 | LEPR_HUMAN | LEPR | Leptin receptor precursor (LEP-R) (OB receptor) (OB-R) (HuB219) (CD295 |
| ENSP00000354769 | Q5T750_HUMAN | | Late envelope protein 7 (LEP7). |
| ENSP00000355364 | FAM5B_HUMAN | FAM5B | Protein FAM5B precursor (BMP/retinoic acid-inducible neural-specific |
| ENSP00000294697 | FAM5C_HUMAN | FAM5C | Protein FAM5C precursor (DBCCR1-like protein 1). |
| ENSP00000356236 | SYT2_HUMAN | SYT2 | Synaptotagmin-2 (Synaptotagmin II) (SytII) |
| ENSP00000296097 | DNJ5G_HUMAN | DNAJC5G | DnaJ homolog subfamily C member 5G (Gamma cysteine string protein) |
| ENSP00000354988 | Q8NBL2_HUMAN | | CDNA PSEC0134 fis, clone PLACE1004757 |
| ENSP00000355121 | NP_848590.3 | | hypothetical protein LOC150771 isoform 1 |
| ENSP00000259241 | H6ST1_HUMAN | HS6ST1 | Heparan-sulfate 6-O-sulfotransferase 1 (EC 2.8.2.—) (HS6ST-1) |
| ENSP00000295738 | NP_653313.2 | | solute carrier family 23 (nucleobase transporters), member 3 |
| ENSP00000327594 | CO4A3_HUMAN | COL4A3 | Collagen alpha-3(IV) chain precursor (Goodpasture antigen) |
| ENSP00000323096 | AMGO3_HUMAN | AMIGO3 | Amphoterin-induced protein 3 precursor (AMIGO-3) (Alivin-3) |
| ENSP00000345667 | Q86SU0-3 | ILDR1 | Immunoglobulin-like domain-containing receptor 1 precursor |
| ENSP00000372402 | Q6ZQR7_HUMAN | CRIPAK | cysteine-rich PAK1 inhibitor, CDNA FLJ45978 fis, clone PROST2007444 |
| ENSP00000323596 | Q9NRB6_HUMAN | FGFR3 | Mutant fibroblast growth factor receptor 3 |
| ENSP00000372328 | Q5GMH4_HUMAN | | Hypothetical protein DKFZp566H184 |
| ENSP00000320793 | 441019 | | |
| ENSP00000330525 | 441019 | | |
| ENSP00000373695 | Q9P273_HUMAN | ODZ3 | Teneurin-3 (Ten-3) (Tenascin-M3) (Ten-m3) (Protein Odd Oz/ten-m homolog 3). |
| ENSP00000274170 | CAD18_HUMAN | CDH18 | Cadherin-18 precursor (Cadherin-14) |
| ENSP00000322211 | Q9BT67-2 | NDFIP1 | NEDD4 family-interacting protein 1 (Breast cancer-associated protein SGA-1M). |
| ENSP00000373555 | Q9NT68_HUMAN | ODZ2 | Teneurin-2 (Ten-2) (Tenascin-M2) (Ten-m2) (Protein Odd Oz/ten-m homolog 2) |
| ENSP00000366412 | Q59F30_HUMAN | FGFR4 | fibroblast growth factor receptor 4 |
| ENSP00000347393 | LAMA2_HUMAN | LAMA2 | Laminin subunit alpha-2 precursor (Laminin M chain) (Merosin heavy |
| ENSP00000356208 | FBX5_HUMAN | FBXO5 | F-box only protein 5 (Early mitotic inhibitor 1) |
| ENSP00000356194 | RGS17_HUMAN | RGS17 | Regulator of G-protein signaling 17 (RGS17) |

TABLE 1-continued

Human Genes Containing Sequence Motif for CxCxxxxCxC-Metal (SEQ ID NO: 38) Binding Loop and Aliphatic Repeat Groups

| EnsemblPeptide_ID | ID | Gene | Description |
| --- | --- | --- | --- |
| ENSP00000369936 | Q9UMK5_HUMAN | ELN | Elastin |
| ENSP00000205386 | NM_007356.1 | | *Homo sapiens* laminin, beta 4 (LAMB4), mRNA |
| ENSP00000353120 | Q6ZS87_HUMAN | | CDNA FLJ45737 fis, clone JCMLC2002751, weakly similar to Von Willebrand factor |
| ENSP00000262089 | Q76B61_HUMAN | SSPO | SCO-spondin homolog (*Bos taurus*), protein coding |
| ENSP00000344630 | O76081-2 | RGS20 | regulator of G-protein signalling 20 |
| ENSP00000373980 | NP_001008495.1 | | transmembrane protein 64 |
| ENSP00000348109 | Q71RG6_HUMAN | | |
| ENSP00000265922 | FAM5A_HUMAN | FAM5A | Protein FAM5A precursor (Deleted in bladder cancer 1 protein) |
| ENSP00000363075 | O60477-2 | DBC1 | Deleted in bladder cancer protein 1 precursor - duplicate of FAM5A above |
| ENSP00000351967 | NP_945352.1 | | Hypothetical protein LOC375791 |
| ENSP00000259271 | DCE2_HUMAN | GAD2 | Glutamate decarboxylase 2 (EC 4.1.1.15) (Glutamate decarboxylase 65 |
| ENSP00000347942 | Q9UQV8_HUMAN | RET | Ret protein precursor, ret proto-oncogene (multiple endocrine neoplasia and medullary thyroid carcinoma 1, Hirschsprung disease) |
| ENSP00000371696 | Q2TUQ5_HUMAN | | Mucin-6 precursor |
| ENSP00000351956 | MUC2_HUMAN | MUC2 | Mucin-2 precursor (Intestinal mucin-2) |
| ENSP00000343037 | MUC5B_HUMAN | MUC5B | Mucin-5B precursor (Mucin-5 subtype B, tracheobronchial) (High |
| ENSP00000341666 | Q6ZRI0_HUMAN | OTOG | CDNA FLJ46346 fis, clone TESTI4047328, moderately similar to *Mus musculus* otogelin |
| ENSP00000310492 | KRA58_HUMAN | | Keratin-associated protein 5-8 (Keratin-associated protein 5.8) |
| ENSP00000374650 | Q9P2P4_HUMAN | | KIAA1302 protein |
| ENSP00000254404 | O15421_HUMAN | NCOR2 | nuclear receptor co-repressor 2 |
| ENSP00000330895 | H6ST3_HUMAN | HS6ST3 | Heparan-sulfate 6-O-sulfotransferase 3 (EC 2.8.2.—) (HS6ST-3) |
| ENSP00000370085 | Q6ZUR6_HUMAN | | CDNA FLJ43399 fis, clone OCBBF2009926. |
| ENSP00000346747 | ENK14_HUMAN | | HERV-K_16p3.3 provirus ancestral Env polyprotein (Envelope |
| ENSP00000219162 | MT4_HUMAN | MT4 | Metallothionein-4 (MT-4) (Metallothionein-IV) (MT-IV) |
| ENSP00000307706 | MT1E_HUMAN | MT1E | Metallothionein-1E (MT-1E) (Metallothionein-IE) (MT-IE) |
| ENSP00000369146 | MT1M_HUMAN | MT1M | Metallothionein-1M (MT-1M) (Metallothionein-IM) (MT-IM) |
| ENSP00000290705 | MT1A_HUMAN | MT1A | Metallothionein-1A (MT-1A) (Metallothionein-IA) (MT-IA) |
| ENSP00000262499 | NP_783319.1 | | Metallothionein M |
| ENSP00000369144 | 441771 | | similar to metallothionein 1G |
| ENSP00000334872 | MT1F_HUMAN | MT1F | Metallothionein-1F (MT-1F) (Metallothionein-IF) (MT-IF) |
| ENSP00000369139 | MT1G_HUMAN | MT1G | Metallothionein-1G (MT-1G) (Metallothionein-IG) (MT-IG) |
| ENSP00000367588 | XR_016086.1 | | CDNA FLJ12986 fis, clone NT2RP3000055 |

TABLE 1-continued

Human Genes Containing Sequence Motif for CxCxxxxCxC-Metal (SEQ ID NO: 38) Binding Loop and Aliphatic Repeat Groups

| EnsemblPeptide_ID | ID | Gene | Description |
| --- | --- | --- | --- |
| ENSP00000330035 | Q9H9U3_HUMAN | | CDNA FLJ12547 fis, clone NT2RM4000634. |
| ENSP00000284168 | NP_689564.3 | | solute carrier family 5 (sodium/glucose cotransporter), member 10 isoform 1 |
| ENSP00000354266 | Q8NA00_HUMAN | | CDNA FLJ36000 fis, clone TESTI2015180 |
| ENSP00000351132 | Q8IXI2-3 | RHOT1 | Mitochondrial Rho GTPase 1, (Ras homolog gene family member T1) (Rac-GTP-binding protein-like protein). |
| ENSP00000346215 | Q8IXI2-4 | RHOT1 | Mitochondrial Rho GTPase 1 (MIRO-1) (hMiro-1) (Ras homolog gene family member T1) (Rac-GTP-binding protein-like protein |
| ENSP00000374311 | LAMA1_HUMAN | LAMA1 | Laminin subunit alpha-1 precursor (Laminin A chain) |
| ENSP00000371515 | Q6ZWI3_HUMAN | | CDNA FLJ41036 fis, clone HLUNG2003872 |
| ENSP00000315894 | Q9H6Z4-4 | RANBP3 | Ran-binding protein 3 (RanBP3) |
| ENSP00000318233 | Q8WYX9_HUMAN | STXBP2 | syntaxin binding protein 2 |
| ENSP00000262627 | Q86X29-2 | LSR | Lipolysis-stimulated lipoprotein receptor |
| ENSP00000366491 | Q6ZTD6_HUMAN | | CDNA FLJ44760 fis, clone BRACE3031579 |
| ENSP00000217422 | ASIP_HUMAN | ASIP | Agouti signaling protein precursor (ASP) (Agouti switch protein) |
| ENSP00000246198 | CT127_HUMAN | C20orf127 | Putative metallothionein C20orf127 |
| ENSP00000362061 | CT111_HUMAN | C20orf111 | Uncharacterized protein C20orf111 |
| ENSP00000342481 | ATP9A_HUMAN | ATP9A | Probable phospholipid-transporting ATPase IIA (EC 3.6.3.1) (ATPase |
| ENSP00000358930 | DNJC5_HUMAN | DNAJC5 | DnaJ homolog subfamily C member 5 (Cysteine string protein) (CSP) |
| ENSP00000348338 | RGS19_HUMAN | RGS19 | Regulator of G-protein signaling 19 (RGS19) (G-alpha-interacting |
| ENSP00000369962 | Q9NSI5_HUMAN | | IGSF5 protein |
| ENSP00000349329 | Q9HAJ0_HUMAN | | CDNA FLJ11556 fis, clone HEMBA1003079 |
| ENSP00000343213 | CLCN5_HUMAN | CLCN5 | Chloride channel protein 5 (ClC-5) |
| ENSP00000354667 | NP_055068.2 | | odz, odd Oz/ten-m homolog 1 |
| ENSP00000324617 | H6ST2_HUMAN | HS6ST2 | Heparan-sulfate 6-O-sulfotransferase 2 (EC 2.8.2.—) (HS6ST-2) |

There are just over one million known and predicted peptide sequences in the prokaryotic genome database (complete genome sequences only), which contains 352 species. Of these peptide sequences, only 158 contain the sequence motif of the present invention. Therefore, less than 0.02% of prokaryote peptides have the sequence motif, whereas almost 0.4% of human peptides contain the sequence motif The Cys-x-Cys-xxxx-Cys-x-Cys (SEQ ID NO: 38) sequence motif appears, therefore, to be prevalent throughout the biological spectrum, being more common in mammals than in prokaryotes.

Table 2 shows the abundance of $CxCx_{(4-6)}CxC$ (SEQ ID NO: 1)-containing peptides from complete genome sequence databases.

TABLE 2

Abundance of $CxCx_{(4-6)}CxC$ (SEQ ID NO: 1) containing peptides from complete genome sequence databases

| Species | Total Peptides | Peptides with $CXCX_{4-6}CXC$[b] (SEQ ID NO. 1) |
|---|---|---|
| Anopheles | 13,639 | 44 |
| Arabidopsis | 31,283 | 28 |
| Bos | 28,584 | 71 |
| Caenorhabditis | 26,439 | 38 |
| Ciona | 20,150 | 37 |
| Danio | 36,065 | 137 |
| Drosophila | 19,789 | 44 |
| Gallus | 24,168 | 59 |
| Homo | 48,403 | 95 |
| Mus | 31,302 | 100 |
| Rattus | 33,745 | 126 |
| Saccharomyces | 6,680 | 7 |
| Takifugu | 22,102 | 65 |
| Tetraodon | 28,005 | 289 |
| Xenopus | 28,324 | 71 |
| All prokaryotes (352 species/strains) | 1,071,513 | 158 |

(a) Known and predicted peptide sequences. Includes multiple peptides derived from the same gene, and likely contains false-positive gene predictions.
[b]Includes mostly unique genes. An attempt was made to remove duplicates and multiple peptides from the same gene.

Table 3 shows examples of protein families with the $CxCx_{(4-6)}CxC$ (SEQ ID NO: 1) motif.

TABLE 3

Examples of protein families with the $CxCx_{(4,6)}CxC$ (SEQ ID NO: 1) motif

| Protein Family | Domain | Consensus Sequence |
|---|---|---|
| Putative negative transcriptional regulator-copper transport operon (CopY) | Bacterial | CNCLPGQCHC (SEQ ID NO: 14) |
| Bacterial S-adenosyl-methyl transferase (SAM) | Bacterial | CxCPxxxPxCxC (SEQ ID NO: 15) |
| Arabidopsis methyl transferase | Plant | CxCPxxx PxCxC (SEQ ID NO: 15) |
| Transcriptional Regulator, MerR family protein | Bacterial | CTCPSIDACTC (SEQ ID NO: 16) |
| Archaean helicase | Archaean | CKCRDSPFCGC (SEQ ID NO: 17) |
| Glutamic acid decarboxylase (GAD) | Eukaryotic | CxCxxQKPCxC (SEQ ID NO: 18) |
| Protein FAM precursor (BMP/retinoic acid-inducible neural-specific (FAM) | Eukaryotic | CQCGPKFPECNC (SEQ ID NO: 19) |
| Heparin-sulfate 6-sulfotransferase(HS6ST) | Eukaryotic | CDCRPGQKKCTC (SEQ ID NO: 20) |
| Teneurin-3(Ten-3) (Tenascin-M3)(Protein Odd Oz/ten-m homolog 3) (ODZ) | Eukaryotic | CDCKNDANCDC (SEQ ID NO: 21) |
| Phospholipid-transporting ATPase IIA (ATP9IIA) | Eukaryotic | CQCPAVVCCRC (SEQ ID NO: 22) |

The consensus sequences for each of the protein families were created through cross-species alignments followed by analysis using programs such as MEME and WebLogo. The motif is found across all three domains of life in a wide variety of proteins. The spacing between the second and third cysteines varies, but often contains a proline, suggesting a loop structure.

Table 4 shows some an example of the evolutionary history of $CxCx_{(4-6)}CxC$- (SEQ ID NO: 1) containing proteins. The presence of the $CxCx_{(4-6)}CxC$ (SEQ ID NO: 1) motif is restricted to a few phylogenic lineages of the widespread S-adenosyl-methyl-transferase (SAM) protein.

Table 4.   Example of evolutionary history of $CxCx_{(4-6)}CxC$ (SEQ ID NO: 1)-containing proteins.

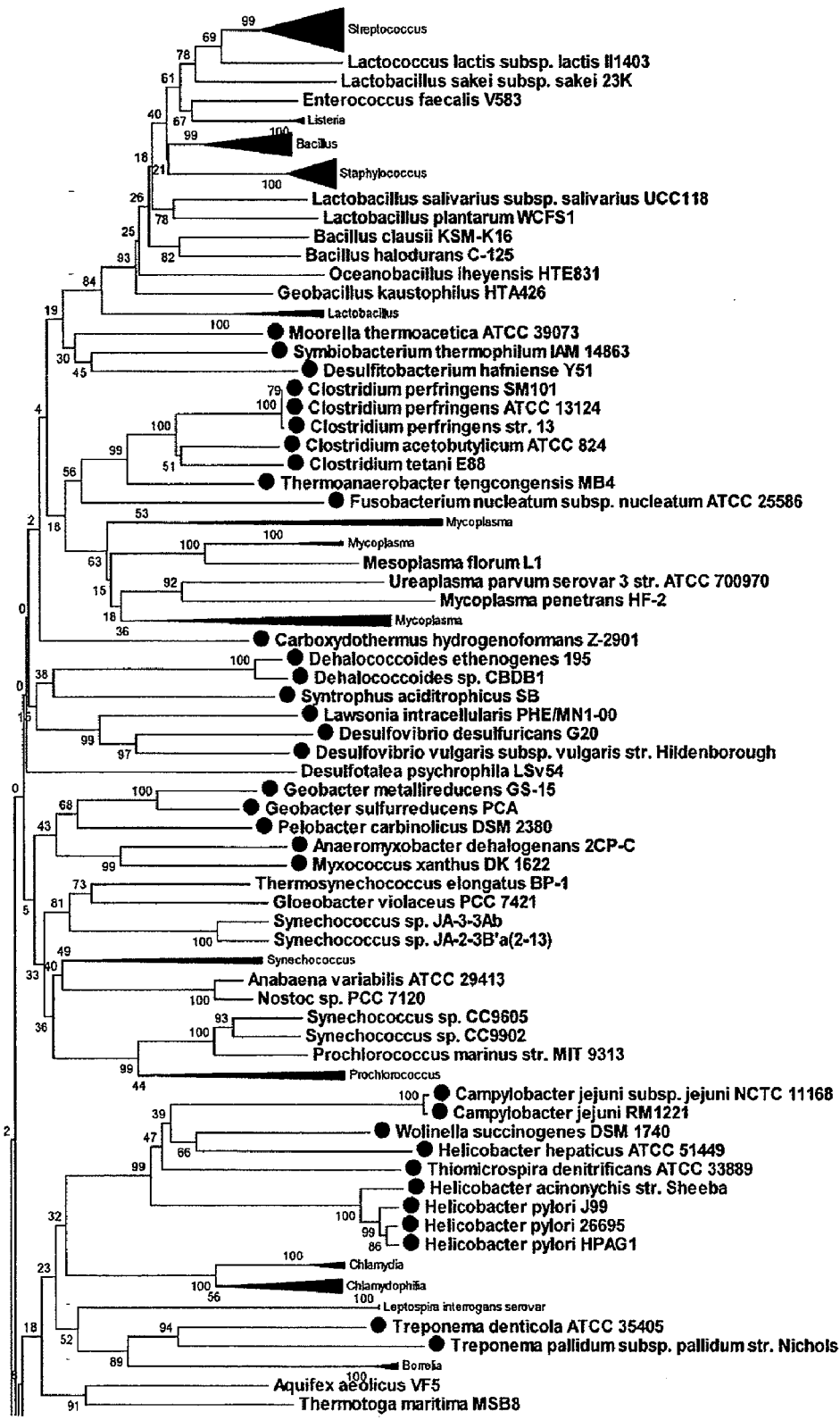

Table 5 shows another example of the evolutionary history of CxCx$_{(4-6)}$CxC (SEQ ID NO: 1)-containing proteins. The CxCx$_{(4-6)}$CxC (SEQ ID NO: 1) motif is conserved in the Eukaryotic Heparan-sulfate-6-sulfotransferase family from humans to worms.

Table 5. Another example of evolutionary history of CxCx$_{(4-6)}$CxC-(SEQ ID NO: 1) containing proteins
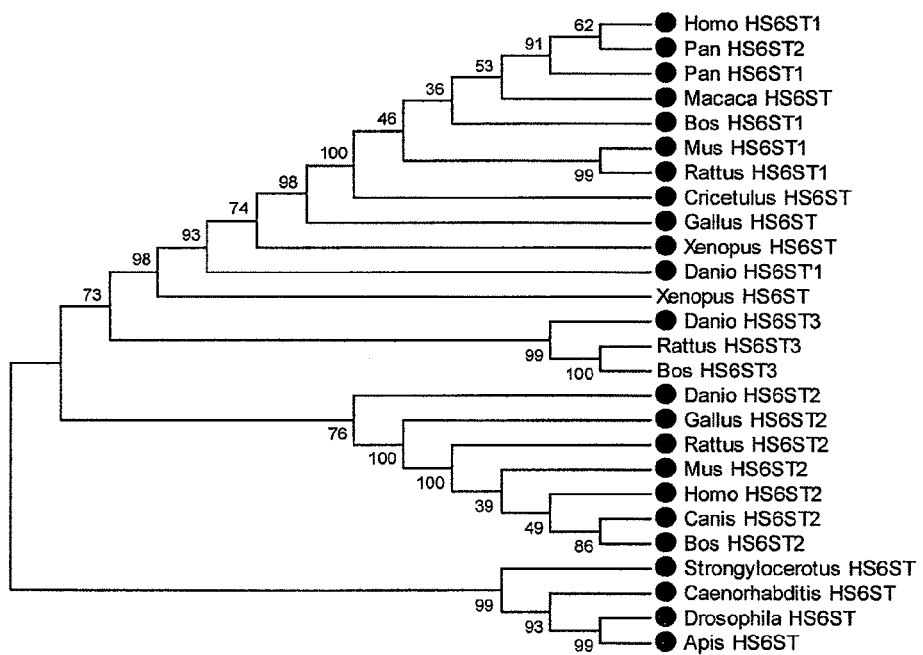

Example

The following example is intended to illustrate the invention, and should not be construed as limiting the invention in any way.

The CopY Dimerization Mechanism

Introduction

This investigation was undertaken to thoroughly assess the role of Zn(II) binding in the CopY metal binding site and to uncover a complete picture of the CopY dimerization mechanism.

CopY is a copper-responsive homo dimeric repressor protein that is known to bind to the DNA of the promoter region of the "cop operon" (Strausak, D. et al., J. Biol. Chem., 272:8932-8936, 1997). Each monomer requires a single four coordinate Zn(II) for DNA binding activity. Each Zn(II) is ligated by the thiolates in a characteristic -Cys-x-Cys-xxxx-Cys-x-Cys (SEQ ID NO: 38)-metal binding site. Under conditions of elevated copper concentrations the copper ions themselves are involved in activation of the cop operon which ultimately leads to a reduction in cell copper levels. The copper chaperone, CopZ, specifically interacts with and delivers Cu(I) to CopY. Two Cu(I) ions displace the single Zn(II) in the CopY metal binding site and adopt three coordinate trigonal planar arrangements with bridging thiolates. When the two Cu(I) ions displace the Zn(II), a conformational change is induced in the protein that decreases its affinity for the promoter, which then allows for the production of copper homeostasis proteins encoded by the genes of the cop operon.

In addition to the carboxy-terminal -Cys-x-Cys-xxxx-Cys-x-Cys (SEQ ID NO: 38)-metal binding motif, CopY also has a series of aliphatic leucine and isoleucine residues that are arranged in a sequence that is similar, but not identical, to the well known leucine zipper motif. Previous studies have indicated that metal binding was critical to the dimerization of the protein, but the contribution of the aliphatic repeat sequence has, up to now, not been investigated.

Subsequent dissection of the potential binding motifs of CopY was afforded through the construction of a CopY truncate fused to a monomeric protein. Bioinformatics analyses and homology models of CopY, combined with ultracentrifugation analyses, suggested that the dimerization motif resides in the C-terminal portion of the protein along with the metal binding motif. The first 70 residues of CopY are very homologous to the Cro repressor. The last 70 residues have two sequences that are likely to form alpha-helices and the -Cys-x-Cys-xxxx-Cys-x-Cys- (SEQ ID NO: 38) at the extreme C-terminus. A BLAST homology search identified 73 bacterial proteins with sequence similarity to *E. hirae* CopY. Homologous proteins possessing the CxCx$_{(4-6)}$CxC (SEQ ID NO: 1) motif are restricted to the Lactobacillales (predominantly *Enterococcus, Lactococcus*, and *Streptococcus*), cluster phylogenetically, and are found within a larger cluster of known and putative transcription repressors, but which contain only three of the four cysteines in the motif. In turn, these proteins group with the large family of DNA-binding repressors, including the beta-lactamase (i.e., penicillinase) and methicillinase repressors. Multiple sequence alignment (not shown) reveals that the CopY peptides share conservation with these latter repressors in the amino terminus, DNA-binding domain; and no similarity in the region containing the CxCx$_{(4-6)}$CxC (SEQ ID NO: 1) motif, consistent with that previously found with a smaller dataset (Solioz, M. et al., FEMS Microbiology Reviews, 27:183-195, 2003).

Significantly, there is a short sequence in the last 40 residues that contains a predicted alpha helix, just prior to metal binding site, which contains a hydrophobic repeat reminiscent of a leucine zipper. A truncate of the last 39 residues previously was shown to dimerize but it was determined to be a poor NMR candidate (Cobine, P., et al., Biochemistry, 41:5822-5829, 2002). To stabilize the sequence and to further understand what forces contribute to the dimerization process, a synthetic gene was been designed that fused the DNA sequence encoding for the C-terminal 38 residues of CopY (Ymbs38) to the gene of the protein GB1. GB1 is the 56-residue immunoglobulin binding domain of streptococcal protein G. The domain is a highly soluble, stable 56-residue monomeric protein that has been extensively characterized by NMR both directly and as a platform for smaller, less structured, peptides. Ultracentrifugational analyses indicate that the metal is essential to the overall dimer stability. Correspondingly, because CopY is not easy to purify and to maintain due to inherent solubility problems, a truncate was construction that enabled a more efficacious investigation of the monomer-dimer dissociation. Large zone gel filtration chromatography was employed to demonstrate the ability of the GB1-CopY C-terminus to promote dimerization.

The goal of these studies, therefore, was to determine the structural features of the C-terminus of CopY that foster dimer formation and determine the effect of metal binding on the dimerization. Furthermore, the role of the widely distributed motif has been explored in other proteins and organisms to explore its evolution and involvement in other proteins.

Materials and Methods

1. General Molecular Biology Methods a. DNA Purification

Promega Wizard® Plasmid DNA MiniPreps were used to extract and purify plasmid DNA from cell cultures. Briefly, the cell pellet was harvested by centrifugation at 5,000×g for 10 minutes from a 5 mL bacterial cell culture. The cell pellet was resuspended in 300 μL of 50 mM Tris, pH 7.5, 10 mM EDTA, 100 μg/mL RNase A. The cells were lysed by addition of 300 μL of a 0.2 M NaOH/1% SDS solution, then neutralized with 300 μL of 1.32 M potassium acetate, pH 4.8. After removal of debris by centrifugation at 10,000×g for 5 minutes, the cleared lysate was applied to 1 mL of the silica-based Wizard® Miniprep DNA Purification resin, which binds the plasmid DNA. The resin was washed through the syringe-driven system with 2 mL of 80 mM potassium acetate, 8.3 M Tris, pH 7.5, 40 μM EDTA, 55% ethanol, and the final purified DNA was eluted by centrifugation at 10,000×g for 30 seconds with a 50 μL aliquot of sterilized deionized H$_2$O. Purity of the plasmid DNA was assessed by measuring the ratio of absorbance at 260 nm to that at 280 nm, with a ratio in the range of 1.8-2.0 considered to be pure (free of contaminating protein or RNA). The concentration of DNA was determined from the absorbance at 260 nm. An $A_{260}$ value of 1 corresponds to a DNA concentration of 50 μg/mL. The DNA concentration was calculated by the following equation: [DNA]=A260× dilution factor×50 μg/mL.

b. Cloning of Genes into Plasmid DNA

Gene fragments of interest were isolated by restriction digests followed by electrophoresis on horizontal agarose gels. The Stratagene StrataPrep® DNA Gel Extraction Kit, which also employs a silica-based matrix to bind DNA, was used to remove the DNA fragment from the agarose gel. The expression vector into which the fragment would be inserted was likewise digested and isolated. The insert and vector were mixed with 1.5 U of T4 DNA ligase (Fisher), incubated at 22°

C. for 3.5 hours, and transformed into competent cells. Single colonies appearing on the antibiotic selective media plates were screened for the presence of the desired insert by restriction digest mapping.

c. Competent Cells

Most experiments utilized competent cells that were purchased from Novagen. Strains that were used included BL21, BL21(DE3), HMS174, and HMS174(DE3). Competent cells also were prepared in the laboratory by the rubidium chloride method. A 2 mL aliquot of a saturated overnight cell culture was added to 200 mL of 1×LB media. The cell culture was incubated at 37° C., while shaking on an orbit shaker at 250 rpm, to an $OD_{600}$=0.3-0.4. The cell culture then was removed from the incubator and placed on ice for 5 minutes. Cells were harvested by centrifugation at 3700×g for 10 minutes, then resuspended in 80 mL of 30 mM potassium acetate, pH 5.8, 10 mM rubidium chloride, 10 mM calcium chloride •$2H_2O$, 50 mM manganese chloride, 15% (v/v) glycerol that had been 0.22 μm filter sterilized. The resuspended cells were incubated on ice for 1 hour, then centrifuged at 4000×g for 10 minutes. The cell pellet again was resuspended in 8 mL of 10 mM MOPS, pH 6.5, 75 mM calcium chloride, 10 mM rubidium chloride, 15% (v/v) glycerol (0.22 μm filter sterilized), and incubated on ice for 3 hours. The resuspended cells then were prepared for storage by aliquoting into 200 μL portions in 1.5 mL sterilized microfuge tubes, and "snap-freezing" in an ethanol-dry ice bath. Competent cells were stored in the −80° C. freezer.

d. Site-Directed Mutagenesis

The Stratagene QuikChange® Site-Directed Mutagenesis Kit was utilized for all mutagenesis experiments. The kit used a PCR-based procedure, in which oligonucleotide primers containing specific point mutations annealed to complementary strands of the parental plasmid and were extended by PfuTurbo DNA polymerase. A mutated plasmid was amplified, the original parental DNA was eliminated by digestion with DpnI restriction enzyme, which specifically digested methylated DNA, and the final mutant plasmid was transformed into XL-1 Blue Supercompetent cells. Mutagenesis oligonucleotide primers were designed with the aid of the Clone Manager Professional Suite software (Scientific & Educational Software). The software allowed for identification of mutagenesis primers that adhered to the specific criteria suggested by the QuikChange kit. Specifically, primers were required to be 25-50 nucleotide bases in length and have a GC content of at least 40%. All acceptable primers had a melting temperature of at least 60° C. Mutagenesis primers typically were designed with an additional change to create a restriction enzyme recognition site that facilitated identification of positive mutants. Positive mutants also were verified by automated dideoxy DNA sequencing carried out at the DNA Sequencing Core Facility of the University of Pittsburgh Biomedical Research Support Facility. Sequencing primers were customized to the specific plasmid vector.

e. Cell Transformation

Plasmid DNA was transformed into competent BL21, BL21(DE3), HMS174, and HMS174(DE3) cells (Novagen) or XL-1 Blue Supercompetent cells (Stratagene). In general, a 20 μL aliquot of competent cells was thawed on ice and 1 μL of plasmid DNA was added directly to the cells. The cells were incubated on ice for 5 minutes, then heat shocked at 42° C. for 30 seconds. After a two minute incubation on ice, 80 μL of SOC growth medium was added to the cells, and the mixture was incubated at 37° C. while shaking on an orbit shaker platform at 250 rpm for 1 hour to allow for cell outgrowth. The cells then were spread onto Luria-Bertani (LB) agar plates supplemented with appropriate antibiotics and incubated at 37° C. overnight (15-18 hours). Single colonies were transferred from the plate into 5 mL of LB+antibiotic growth media and subsequently screened for incorporation of the desired plasmid DNA.

f. Liquid Media for Growth of *E. coli*

Luria-Bertani (LB) medium was used for most cell cultures. One liter of 5× concentrated media was made by mixing 50 g of tryptone, 25 g of yeast extract, and 25 g of NaCl in 1 L of Milli-Q® deionized water. Sterilization of the media was achieved by autoclaving. The 1× concentrated LB media used for cell cultures was prepared by diluting 200 mL of the 10× concentrated solution with 800 mL of sterilized Milli-Q® deionized water. The pH of the 1×LB media was adjusted to approximately 7.0 by the addition of 1 mL of 1 M NaOH prior to use (126).

Terrific Broth was used to obtain higher cell yields of cells that were transformed with the pWH6 plasmid (for expression of the 6× histidine tagged (SEQ ID NO: 37) CopY). One liter of 5× concentrated Terrific Broth was prepared by mixing 60 g of tryptone, 120 g of yeast extract and 20 mL of glycerol in 1 L of Milli-Q® deionized water. The media was sterilized by autoclaving. The 1× concentration Terrific Broth media was prepared by mixing 200 mL of the 5× concentrated solution with 100 mL of a sterilized 0.17 M $KH_2PO_4$, 0.72 M $K_2HPO_4$ solution, and diluting the final solution up to 1 L with Milli-Q® deionized water (126).

2. Plasmid Constructs of Expressed Proteins a. Histidine-Tagged CopY

A plasmid containing the gene for the histidine tagged CopY was provided by Professor Marc Solioz. The CopY gene was cloned into a Qiagen pQE8 vector by ligation at BamHI and HindIII restriction enzyme sites. The resulting pWH6 plasmid construct encoded a CopY protein with a 6× His tag (SEQ ID NO: 37) attached to the N-terminus. The plasmid also allowed for induction of protein expression by isopropyl-β-D-thiogalactopyranoside (IPTG), and provided antibiotic resistance to ampicillin to allow for selection of cells containing the construct. A plasmid map is shown in FIG. 6. Genes of interest are denoted by arrows. The direction of transcription is indicated by the direction of the arrow. "Amp-R" encodes β-lactamase, which confers ampicillin resistance. "6hCopY" encodes the 6× his tagged (SEQ ID NO: 37) CopY. "Cm-R" confers resistance to chloramphenicol. Locations at which restriction enzymes cleave the DNA are indicated around the outside of the plasmid map. All restriction enzymes shown are single cutters. The origin of replication is located at base pair position 2533.

b. Wild-Type (Untagged) CopY

A plasmid containing the gene for the CopY was provided by Professor Marc Solioz. The CopY gene was cloned into a Qiagen pQE12 vector by ligation at BamHI and HindIII restriction enzyme sites. Site-directed mutagenesis was required to remove 5 N-terminal amino acid residues that originated from the vector sequence. The resulting pWY145 plasmid construct allowed for induction of protein expression by IPTG and provided antibiotic selection by ampicillin. The plasmid map is shown in FIG. 7. Genes of interest are denoted by arrows. The direction of transcription is indicated by the direction of the arrow. "Amp-R" encodes β-lactamase, which confers ampicillin resistance. "CopY" encodes the CopY gene. Locations at which restriction enzymes cleave the DNA are indicated around the outside of the plasmid map.

c. GB1-Ymbs38 Fusion Protein

A 294 base pair synthetic gene encoding the sequence of the GB1 protein and the C-terminal 38 amino acids of CopY was purchased from GenScript™ Corporation. The codon usage was optimized by GenScript™ for protein expression in *E. coli*. The sequence of the synthetic gene, as well as the translated fusion protein sequence, are shown in FIG. 8. The DNA sequence of the synthetic gene that encodes for the GB1-Ymbs38 fusion protein is shown in black text. The translated fusion protein is shown in green text, with the GB1 segment denoted by a red underline, and the Ymbs38 portion denoted by a purple underline. Key restriction enzyme sites are shown in blue text.

GenScript cloned the synthesized gene into a pUC57 plasmid vector and the final construct was received in lyophilized from. After reconstitution in sterile deionized $H_2O$, the DNA was transformed into HMS174 Competent Cells, spread on LB agar plates containing 100 µg/mL ampicillin and incubated at 37° C. overnight. Single colonies were screened by restriction mapping of the purified plasmid DNA. To facilitate purification of the fusion protein, it was preferred that a 6× his tag (SEQ ID NO: 37) be attached to the N-terminus of the protein. The pUC57 construct was digested with NdeI and HindIII restriction enzymes to excise the GB1-Ymbs38 gene. The gene fragment was ligated to pET-14b that had been digested with the same enzymes. Ligation was carried out at 22° C. for 3.5 hours with 1.5 U of T4 DNA ligase. The pET-14b vector attaches a 6× his tag (SEQ ID NO: 37) to the N-terminus and also includes a thrombin protease site between the 6× his tag (SEQ ID NO: 37) and the N-terminus to allow for easy removal of the 6× his tag (SEQ ID NO: 37) after purification. The final plasmid construct is shown in FIG. 9. Genes of interest are denoted by arrows. The direction of transcription is indicated by the direction of the arrow. "Amp-R" encodes β-lactamase, which confers ampicillin resistance. "6hGB1-Ymbs38" encodes the 6× his tagged (SEQ ID NO: 37) fusion protein. Restriction enzymes that cleave the DNA at a single location are shown around the outside of the plasmid. The origin of replication is located at base pair position 2681.

3. Protein Purification a. SDS-PAGE

SDS-polyacrylamide gel electrophoresis was carried out according to the Tris-tricine system described by Schaegger, H. et al. (Analytical Biochemistry, 166:368-379, 1987). Separating gels were 15% acrylamide with a 6% stacking gel. Protein samples were diluted 1:1 with sample buffer (0.1 mM Tris, pH 6.8, 1% (w/v) {SDS, 5% (v/v) β-mercaptoethanol, 24% (v/v) glycerol, 0.02% (w/v) Coomassie Blue G-250) and heated at 100° C. for 5 minutes. Protein samples were electrophoresed at 200 V, followed by staining with 0.25% (w/v) Coomassie Brilliant Blue R-250 prepared in 25% (v/v) isopropanol and 10% (v/v) acetic acid, and destaining with 7.5% (v/v) methanol, 10% (v/v) acetic acid.

b. Histidine-Tagged CopY

Large (4-6 L) cell cultures of BL21(DE3) competent cells transformed with the pWH6 plasmid were grown at 37° C. on an orbit shaker platform at 250 rpm, to an $OD_{600}$ of 0.6-1.0 in either LB or Terrific media containing 100 µg/mL ampicillin. Large cultures were typically grown in 8-12 two-liter flasks containing 500 mL of the LB (or Terrific)+amp media. Protein expression was induced with 1.5 mM IPTG. Immediately after induction, the growth media was supplemented with 0.5 mM $ZnSO_4$ and cell cultures were incubated for an additional 2 hours. Centrifugation at 5,000×g for 10 minutes isolated a cell pellet, which was stored at −20° C. The cell pellet was resuspended in 2 mL of lysis buffer (50 mM Tris, pH 8.0, 50 mM NaCl, 10% sucrose, 0.01% mercaptoethanol) per gram of cells, and incubated on ice with lysozyme (0.4 mg/mL cells) for 1 hour. Cells were lysed by sonicating for six 30-second bursts. Centrifugation at 39,100×g (18,000 rpm in an SS-34 rotor) for 30 minutes at 4° C. removed the cell debris.

The supernatant, containing the soluble his-tagged CopY, was diluted 1:1 with 50 mM Tris, pH7.8, 300 mM NaCl (Buffer A), then loaded onto a 1.5 mL Sigma® His-Select™ Nickel Affinity column equilibrated in the same buffer. All column chromatography steps were carried out at 4° C. After loading, the column was washed with Buffer A until $A_{280}$<0.05, followed by protein elution of the tagged CopY with a 0-100% gradient over 80 mL of 250 mM imidazole in Buffer A. Alternatively, the protein was eluted with a direct application of 250 mM imidazole in Buffer A. Purity of the 6× his-tagged (SEQ ID NO: 37) CopY was analyzed by SDS-PAGE. Contaminating proteins were removed by a second pass through the His-Select™ resin (after removal of imidazole from the protein sample by dialysis) or by separation on a HiLoad 26/60 XK Superdex 75 column (Pharmacia) equilibrated in 50 mM Tris, pH 7.8, 150 mM NaCl. Concentration of the protein was determined by the absorbance at 280 nm, using a previously determined molar extinction coefficient of 27,000 $M^{-1}cm^{-1}$. The value for concentration obtained by this method was verified by comparison to the zinc concentration as indicated by Flame Atomic Absorption Spectrophotometry (FAAS) and by measurement of thiol (—SH) content by the 2,2'-dithiodipyridine (DTDP) assay (Grassetti, D. R. et al., Arch. Biochem. Biophys., 119:41-49, 1967).

c. Wild-Type (Untagged) CopY

Large 4-6 L cell cultures of BL21(DE3) competent cells transformed with the pWY145 plasmid were grown at 37° C., with shaking on an orbit shaker platform at 250 rpm, in LB media containing 100 µg/mL ampicillin. Protein expression was induced by the addition of 1.5 mM IPTG and 0.5 mM $ZnSO_4$ at an $OD_{600}$=0.6-1.0. Following an additional 2 hours of incubation, cells were harvested by centrifugation at 5000×g for 10 minutes, and the cell pellet was stored at −20° C. The cell pellet was resuspended in 50 mM Tris, pH 7.8, 10% sucrose (2 mL/g of cells), and incubated for 30 minutes on ice with 0.4 mg/mL lysozyme. The cells were lysed by six 30-second bursts with a sonicator, and were centrifuged at 39,100×g for 30 minutes (4° C.). The supernatant was passed through a DEAE Fractogel® (Merck Chemicals Ltd.) column run at 4° C. and equilibrated with 50 mM Tris, pH 7.8. The column was washed with this buffer until $A_{280}$<0.05. CopY was eluted with a 0-0.5 M NaCl gradient over 340 mL in 50 mM Tris, pH 7.8 buffer. Fractions containing CopY were pooled, concentrated in an ultrafiltration device (Amicon) fitted with a 10,000 molecular weight cut-off membrane, and passed through a HiLoad 26/60 XK Superdex 75 gel filtration column (Pharmacia) run at 4° C. in 50 mM Tris, pH 7.8, 150 mM NaCl buffer. The fractions into which CopY eluted were determined by the presence of zinc as measured by FAAS. Purity of CopY was assessed by SDS-PAGE. The concentration of CopY was determined by measuring $A_{280}$, using 27,000 $M^{-1}cm^{-1}$ for the molar extinction coefficient (81, 105). The concentration was confirmed by comparison to the zinc concentration measured by FAAS and the thiol concentration by the DTDP assay.

c. GB1-Ymbs38 Fusion Protein

The pKOPGY38 plasmid was transformed into HMS174 (DE3) competent cells and induction tests were carried out to ensure the protein would be adequately expressed in the cell line. Large 4-6 L cell cultures were grown in LB+ampicillin broth at 37° C. and 250 rpm from colonies that exhibited sufficient expression. Protein expression was induced by addition of 1.5 mM IPTG and 0.5 mM $ZnSO_4$ at an $OD_{600}$ of 0.6-1.0. After a 2 hour induction incubation, cells were harvested by centrifugation at 5000×g for 10 minutes and stored at −20° C. The cell pellet was resuspended in 50 mM Tris, pH 8.0, 50 mM NaCl, 10% sucrose, 0.01% β-ME (2 mL/g of cells) and incubated on ice for 1 hour with lysozyme (0.4 mg/mL cells). The suspension was sonicated (six 30-second bursts) to enhance lysis of the cells and then was centrifuged at 34,800×g for 30 minutes in an SS-34 rotor. The supernatant was diluted 1:1 with 50 mM Tris, pH 7.8, 300 mM NaCl. The entire sample was purified on a 1.5 mL Sigma® His-Select™ Nickel Affinity column at 4° C. as described above for the his-tagged CopY. The GB1-Ymbs38 protein purified in this manner was estimated to be >90% pure by analysis on an SDS-PAGE gel. Analysis of the protein by flame atomic absorption spectroscopy showed that the protein purified as a Zn-binding protein. Comparison of the zinc concentration to the concentration of thiols as determined by the DTDP assay resulted in a ratio of 3.8 thiols per Zn.

4. Preparation of apo Protein a. EDTA Treatment (Non-Denaturing Preparation)

Pure proteins were treated with 125 mM EDTA to strip the metal and 150 mM DTT to reduce the free thiols. After a 30 minute incubation at room temperature, the treated proteins were passed through a Sephadex G-25 column equilibrated in 50 mM Tris, pH 7.8, 150 mM NaCl. The reduction state was confirmed by the DTDP assay. All steps were carried out in an Omni-Lab anaerobic glove box (Vacuum Atmospheres Company).

b. Acidification (Denaturing Preparation)

Pure proteins were treated with 6 M guanidine-HCl, 100 mM EDTA and 150 mM DTT. The mixture was incubated at 42° C. for 2 hours, transferred into the Omni-Lab anaerobic glove box and separated on a Sephadex G-25 column equilibrated in 25 mM HCl at room temperature. One mL of 1 M HCl was loaded onto the column immediately before and immediately after protein loading. Reduction of thiols was verified by the DTDP assay. For subsequent experimentation, the pH of the protein solution was increased to 7.8 by the addition of Tris buffer to a final concentration of 0.1 M.

c. Cysteine Modification with Iodoacetamide

Reduced apo proteins in 50 mM Tris, pH 7.8, 150 mM NaCl were treated with 30 mM iodoacetamide in order to covalently modify the cysteinyl thiolates. The modification served the purpose of preventing the thiolates from forming disulfide bonds and from binding any trace metals present in the experimental system. The pH of the solution was kept at 7.8-8.0, and the reaction was incubated in the dark at room temperature inside the Omni-Lab anaerobic glove box for 30 minutes. The reaction mixture was transferred out of the anaerobic glove box, concentrated to approximately 1 mL with an Amicon ultrafiltration device and passed through a Sephadex G-25 size exclusion column to exchange into an appropriate buffer for subsequent experimentation.

5. Metal Titrations a. Copper(I) Titrations

Cu(I) stock solutions were prepared either as a Cu(I) acetonitrile (ACN) perchlorate $(Cu(I)(CH_3CN)_4ClO_4)$ salt dissolved in 60% acetonitrile, or as CuCl dissolved in 1 M NaCl, 0.1 M HCl. In each case, the solid Cu(I) compound was reconstituted into solution under anaerobic conditions. Concentrations of the Cu(I) stock solutions were determined by flame atomic absorption spectroscopy. All titrations were performed inside the Omin-Lab anaerobic glove box. Cu(I) was added to 5 nmol of protein in 2.5 nmol increments (0.5 molar equivalents) into a final volume of 1 mL. Titration samples were transported in anaerobically sealed screw top cuvettes (Spectrocell, Inc.) for spectral analysis outside of the glove box. Titrations were followed by measuring the formation of a S—Cu(I) ligand to metal charge transfer band (LMCT) at 250 nm in the absorption spectrum between 200-420 nm (82) on a Varian Cary 3E spectrophotometer. Titrations also were followed by the fluorescence emission spectrum between 500-700 nm after excitation at 295 nm (26, 82). A Perkin Elmer LS50B spectrophotometer with excitation and emission slit widths set at 5 nm and 20 nm, respectively, was used for all fluorescence measurements. The final copper concentration of each titration sample was verified by FAAS.

b. Cadmium Titrations

Cd(II) stock solutions were prepared as $CdCl_2$ dissolved in 25 mM HCl. The concentration of the stock solution was measured by FAAS. Cd(II) was titrated into 5 nmol of protein in 1.25 nmol increments (0.25 molar equivalents) into a final volume of 1 mL. Titrations were followed by measuring the absorption spectrum between 200-420 nm. The formation of the S—Cd(II) LMCT was followed at 250 nm. Final cadmium concentrations of each titration sample were determined by FAAS.

c. Cobalt Titrations

Co(II) stock solutions were prepared in the Omin-Lab anaerobic glove box as $CoCl_2.6H_2O$ dissolved in 25 mM HCl. The concentration of the stock solution was measured by FAAS. Apo proteins were prepared by either the EDTA treatment or acidification procedures described above. Co(II) was titrated into 87 nmol of apo protein in 0.5 molar equivalent increments into a final volume of 800 μL. Spectral analysis was facilitated by anaerobically sealing the titration sample in a screw top cuvette (Spectrocell). The absorption spectrum between 190-900 nm was measured. The d-d transition bands were observed as absorption peaks at 600 nm, 690 nm, and 765 nm, while the S—Co(II) LMCT were observed at 248 nm, 305 nm, and 367 nm. Following spectral analysis; Co(II)-protein samples were anaerobically transferred to EPR tubes, sealed and frozen by submerging in liquid nitrogen. EPR analysis then was performed on the samples. Perpendicular mode X-band EPR signals were monitored at a temperature of 5.8 K, a microwave frequency of 9.65 GHz and a microwave power of 0.2 mW.

6. Gel Filtration Chromatography-Size Exclusion Chromatography for Molecular Weight Determination A HiLoad 26/60 XK Superdex 75 column (Pharmacia) equilibrated in 50 mM Tris, pH 7.8, 150 mM NaCl, 0.1% β-mercaptoethanol was used for the initial molecular weight estimation of all purified proteins. All chromatographic experiments were carried out at 4° C. Protein elution was followed by measurement of the absorbance at 280 nm or at 220 nm at a flow rate of 2 mL/min. Flow rates were regulated by a Waters Delta 600 HPLC and absorbance was monitored with a Waters 2996 Photodiode Array detector. All Waters HPLC components were interfaced to Millenium$^{32}$ Chromatography Manager Software, Version 4.00. Blue dextran (2000 kDa), bovine serum albumin (66 kDa), ovalbumin (45 kDa), carbonic anhydrase (29 kDa), cytochrome C (12.5 kDa), and aprotinin (6.5 kDa) were used as calibration standards (Sigma). The calibration curve is shown in FIG. 10. Standards include carbonic anhydrase (29 kDa), and cytochrome c (12.5 kDa), and aprotinin (6.5 kDa). Equation of the line: y=−1.10x+6.24, where x=($V_e$ of sample/$V_o$). Void volume $V_o$ was determined from the elution volume of blue dextran=109.4 mL.

7. Large Zone Gel Filtration Chromatography a. Experimental Procedure

The Shodex KW 803 HPLC column, of 15 mL total column volume, was used for all experiments. The column was equilibrated in 50 mM Tris, pH 7.8, 150 mM NaCl, 0.1% β-mercaptoethanol and was run at 4° C. The column was calibrated with Blue dextran (2,000 kDa, used to determine the void volume), bovine serum albumin (66 kDa), ovalbumin (45 kDa), carbonic anhydrase (29 kDa), and RNaseA (13.7 kDa). A standard curve was prepared by plotting the log of the molecular weight of each standard versus the elution volume of each standard divided by the void volume (FIG. 11). Standards include bovine serum albumin (66 kDa), ovalbumin (45 kDa), carbonic anhydrase (29 kDa), and RNase A$^-$ (13.7 kDa). Equation of the line: y=−2.67x+8.80, where x=($V_e$ of sample/$V_o$). Void volume $V_o$ was determined from the elution volume of blue dextran=6.5 mL. Pure protein samples of successively decreasing concentrations were loaded onto the column in 5 mL injection volumes. The flow rate was 1 mL/min. Elution of the protein sample was followed by recording the absorbance trace at 280 nm. First derivative curves of the elution profiles were prepared by plotting the change in absorbance per a 0.025 mL increment of volume (ΔA/ΔV) versus the average volume of the increment.

b. Analysis of Large Zone Chromatography Data

Equilibrium dissociation constants were calculated from the leading edge elution volumes ($V_e$) of the large zone chromatography experiments. The leading edge $V_e$ was taken as the volume at the apex of the leading edge peak in the first derivative curve. The leading edge $V_e$ was converted to the weight average partition coefficient, $\sigma_w$, which gave a measure of the fraction of total column volume that is accessible to the protein solute.

$$\sigma_w=(V_e-V_o)/V_t$$

$V_o$ is the void volume of the column, determined by the elution volume of a small zone injection (100 μL) of blue dextran. $V_t$ is the total column volume, determined by a small zone injection (100 μL) of imidazole. In order to subsequently assess the monomer-dimer equilibrium, the partition coefficients of the entirely dimeric species and the monomeric species must be known. The partition coefficient of the protein dimer was estimated from the $V_e$ of a large zone injection of highly concentrated protein. The partition coefficient of the monomeric species was obtained from the $V_e$ of the lowest concentration of apo protein in which the leucine and isoleucine residues had been mutated to serine, loaded as a large zone. The partition coefficients then can be utilized to calculate the fraction of monomer, $f_m$, in each particular injection sample.

$$f_m=(\sigma_w-\sigma_d)/(\sigma_m-\sigma_d)$$

To obtain the equilibrium association constant, $K_a$, the experimental $f_m$ values are fit, by non-linear least squares analysis, to the monomer-dimer equilibrium model equation.

$$f_m=[-1+(1+(8K_a[C_t]))^{1/2}]/(4K_a[C_t])$$

$C_t$ is the total protein concentration loaded onto the column. The fitting process was performed in Microsoft Excel. Residuals, calculated as the difference between the experimental $f_m$ values and the calculated $f_m$ values from the model equation, were squared. The sum of squares of all the residuals was minimized through the use of the "Solver" analysis tool. The Solver tool was set to minimize the target cell containing the sum of squares value by changing the value of the cell containing an estimated $K_a$ value. Calculating $f_m$ over a range of concentrations by inserting the final $K_a$ value into the model equation allows for a "best fit" curve to be plotted. The best fit curve is plotted as $\sigma_w$ vs. log [$C_t$] and the experimental data points are overlaid to show the extent of conformity. FIG. 12 shows the Excel spreadsheet containing the actual formulas used for the large zone size exclusion chromatography calculations. Formulas were entered into each respective cell using the standard Excel formula language. Columns B and D are numerical values entered by the user after the experimental data are collected. The sum of squares in cell I12 is minimized by changing the value for the equilibrium constant in cell H5. The minimization is accomplished with the Excel Solver tool. The final equilibrium constant is incorporated into the equation in column L to calculate a partition coefficient based on a range of concentrations entered by the use in column K.

FIG. 13 is a sample spreadsheet that shows the numerical calculations for one of the large zone trials with the Zn(II) form of GB1-Ymbs38. The same Excel spreadsheet that is shown in FIG. 12, containing the actual numerical values calculated by the formulas. The experimental values were obtained from a large zone size exclusion chromatography experiment on the Zn(II) form of GB1-Ymbs38.

7. Electrospray-Ionization Mass Spectrometry

A Waters Micromass ZMD quadrupole mass spectrometer was used for all experiments. The mass spectrometer was calibrated with cesium iodide. The temperature at the ion spray interface was kept at 40° C. A voltage of 2.0 kV at the tip of the inlet capillary needle was used to generate the electrospray. The cone voltage was set at 20 V and the extractor voltage was set at 10 V, resulting in a declustering voltage (ΔCS) of 10 V. Samples of protein were prepared in 10 mM ammonium acetate, pH 8.0, at concentrations of approximately 250 μM and were delivered at a flow rate of 50 μL/min into the ion source.

8. Affinity Resin Binding Assay

Sigma® HIS-Select™ Nickel Affinity resin was used to assess dimerization between histidine-tagged and untagged proteins. Tagged and untagged versions of CopY were isolated as described above. The untagged version of GB1-Ymbs38 was isolated from the purified tagged protein by treatment with the Sigma® THROMBIN CleanCleave™ Kit. A thrombin cleavage site between the histidine tag and the start of the GB1-Ymbs38 protein allowed for easy removal of the tag. Dimerization reactions of tagged and untagged protein were performed in 50 mM Tris, pH 7.8, 300 mM NaCl. Approximately equilmolar amounts of each protein were mixed and incubated at 37° C. for 45 minutes to promote subunit interchange. The protein mixture was applied to 100 μL of drained HIS-Select resin that had been equilibrated in 50 mM Tris, pH 7.8, 300 mM NaCl in a Centricep spin column (Princeton Separations, Inc.) at room temperature. After 1 minute of constant agitation, the resin-protein mixture was centrifuged at 500×g for 30 seconds and the flow through was collected in a clean microfuge tube. The resin then was washed twice with 350 μL of 50 mM Tris, pH 7.8, 300 mM NaCl, and once with 50 mM Tris, pH 7.8, 300 mM NaCl, 20 mM imidazole. Each wash step was followed by centrifugation at 500×g for 30 seconds to remove excess liquid. Proteins were eluted from the resin with 50 μL of 50 mM Tris, pH 7.8, 300 mM NaCl, 250 mM imidazole. Eluants were analyzed on 15% Tris-tricine SDS-PAGE stained with Coomassie brilliant blue R-250.

9. Purification and Ultracentrifugation Analysis of ZnCopY and Isolation of CopZ.

ZnCopY and CopZ were isolated as previously described (Cobine, P., et al., Biochemistry, 41:5822-5829, 2002). The isolated CopY had a Zn(II) to protein stoichiometry of 1 to 1. The purified apo-CopZ was reduced and titrated with Cu(I). The purity of both proteins was determined by SDS-PAGE. Sedimentation equilibrium experiments were conducted on metalated forms CopY in Tris-chloride buffer, pH 7.9 in order to ascertain whether the protein behaved as a monomer-dimer in equilibrium. A Beckman XL-I ultracentrifuge operated at 20° C. was used for these experiments. Because of the susceptibility of the CopY sulfhydryl groups to oxidation, the centrifuge cells were assembled and filled anaerobically in a glovebox.

Spectrophotometric records at 230 nm of the resulting sedimentation equilibrium distributions were analyzed in accordance with the expression:

$$A_{230}(r) = A_{230}(0) \exp[M_A(1-\sigma_A \rho_s) \omega^2 r^2 /(2RT)]1 \qquad (1)$$

in which $A_{230}(r)$ is the absorbance at radial distance r in an experiment conducted at angular velocity and absolute temperature T in a buffer with density $\rho_S$. R is the universal gas constant. $A_{230}(0)$ denotes the absorbance at the reference radial position, taken as the center of rotation (R)=0). Nonlinear regression analysis of the radial dependence of $A_{230}$ in terms of equation 1 was used to obtain two curve-fitting parameters: the notional absorbance at the center of rotation and the buoyant molecular mass, $M_A(1-v_A \rho_s)$. To effect the conversion of the latter parameter to a molecular mass ($M_A$) the partial specific volume ($v_A$) of CopY was taken as 0.740 mL/g, deduced from the amino acid composition, whereas the buffer density of 1.0066 g/mL was determined at 20° C. by standard procedures in an Anton-Paar density meter.

Results

The experiments described herein were carried out in an effort to better understand the forces that are contributing to the CopY dimerization process and to potentially obtain a more accurate three-dimensional structure. A fusion protein was designed that joined Ymbs with the protein GB1. The N-terminus of Ymbs was fused to the C-terminus of GB1. GB1 was the immunoglobulin binding domain of the streptococcal protein G. The high stability, solubility, and small size (56 amino acids in length) of GB1 made it an optimal choice for these studies. GB1 was particularly suitable for both dimerization studies and structural analysis of Ymbs because of its known monomeric formation, its inability to bind metal ions, and its extensive structural characterization by NMR methods. This investigation demonstrated that the 38 C-terminal amino acids of CopY were sufficient to promote protein dimerization in addition to serving as a metal binding domain.

1. Size Exclusion Chromatography

To examine the ability of Ymbs38 to initiate self association, the 6× histidine tagged (SEQ ID NO: 37) GB1-Ymbs38 was subjected to size exclusion chromatography on a HiLoad 26/60 Superdex 75 column (Pharmacia) (FIG. 14). GB1-Ymbs38 was loaded onto the Superdex 75 (Pharmacia) at a concentration 90 µM, while GB1 was loaded at a concentration of 84 µM. The chromatography experiments were run in 50 mM Tris, pH 7.8, 150 mM NaCl. Zn(II) GB1-Ymbs38 is shown as a solid red trace, with the major peak eluting at a size of 22.5 kDa. GB1 is shown as a dashed blue trace, with the major peak eluting at 10 kDa. Calculation of apparent molecular weight was accomplished by reference to a standard plot of calibration standards. As shown in FIG. 14, GB1-Ymbs38 migrated with an apparent native molecular weight mass of 22.5 kDa. Considering that the calculated molecular weight of the histidine-tagged protein was approximately 12.8 kDa, the data suggested that the protein exists as a dimer. This conclusion was further supported by comparison of the GB1-Ymbs38 elution profile to that of the 6× histidine tagged (SEQ ID NO: 37) GB1 protein. GB1 subjected to size-exclusion chromatography under the same conditions migrated at an apparent molecular weight of 10 kDa, which corresponded to the calculated molecular weight of 8.4 kDa.

2. Electrospray Ionization Mass Spectrometry

The GB1-Ymbs38 protein was subjected to ESI-MS under gentle focusing conditions. Analysis of non-covalent protein complexes was critically dependent on a small difference between the cone and extractor voltages, termed the declustering voltage ($\Delta$CS). Oligomers formed through non-covalent interactions were more likely to survive the desolvation process if the $\Delta$CS did not exceed 100 V. A $\Delta$CS of 10 V was used for these experiments, with the cone voltage set at 20 V and the extractor voltage at 10 V. A voltage of 2 kV at the tip of the inlet capillary was used to generate the electrospray. The temperature at the ion spray interface was kept at 40° C. Protein samples (approximately 250 µM) were prepared in 10 mM ammonium acetate, pH 8.0. FIG. 15 shows the mass spectrum of the Zn(II)-loaded form of GB1-Ymbs38 acquired under these conditions. Monomer ions are the most abundant, and their charge states are indicated with green numbers. The direct identification of the homodimer complex is represented by the less intense signals indicated with red numbers. The molecular mass derived from the +17 and +19 charged ions is 25,260 Da, while the mass derived from the +9 and +10 charged ions is 12,625 Da. (Calculated monomeric molecular mass of GB1-Ymbs38=12,760 Da.) The deviation of the mass derived from the spectrum from the actual mass is due to a calibration error.

Ion charges and the corresponding molecular masses were calculated from the mass-to-charge ratios detected by the mass spectrometer through the procedure shown in FIG. 16. The two adjacent monomeric ions with charges of +9 and +10 from the mass spectrum of Zn(II) GB1-Ymbs38 (FIG. 3.19) were chosen for this example calculation.

A 6× histidine tagged (SEQ ID NO: 37) version of GB1 alone (lacking the Ymbs38 extension) was subjected to ESI-MS under the same conditions. No charged ions suggestive of higher order species were detected in the GB1 mass spectrum (FIG. 17). Charged ions due to monomeric GB1 are shown labeled with the bolded numbers. The molecular mass derived from the +6 and +7 charge states is 8258 Da. (Calculated molecular mass of GB1 with the 6× histidine tag=8387 Da. (SEQ ID NO: 37)). The result indicated that the 38 C-terminal amino acids of CopY were responsible for the observed dimerization of the GB1-Ymbs38 fusion protein.

The ESI mass spectrum of the apo form of GB1-Ymbs38 allowed for further investigation of the importance of metal binding to the dimerization interaction. Apo-GB1-Ymbs38 was prepared either by stripping the metal with EDTA (non-denaturing treatment) or by acidifying the protein solution (denaturing treatment). The free cysteinyl thiols then were carboxyamidomethylated by reaction with iodoacetamide for the purpose of blocking any potential metal binding and preventing the formation of disulfide bonds. The ESI mass spectrum of apo-GB1-Ymbs38 with modified cysteines did not exhibit any signals that were suggestive of the presence of homodimers (FIG. 18). Monomeric charged ions are labeled with green numbers. The molecular mass derived from the +9 and +10 charge states is 12,865 Da. The carboxyamidomethylation of the four cysteines in the metal binding motif adds a total of 232 Da to the overall molecular mass. (Calculated molecular mass of carboxyamidomethylated GB1-Ymbs38=12,992 Da.). This experiment demonstrated that metal binding is critical to the ability of GB1-Ymbs38 to dimerize.

3. HIS-Select™ Affinity Resin Binding Assay

To further examine the dimerization of the GB1-Ymbs38 protein, an affinity resin binding assay was used. The pET-14b expression vector (Novagen), into which the gene for GB1-Ymbs38 was cloned, encoded for a thrombin cleavage site between the 6× histidine tag (SEQ ID NO: 37) and the start of the protein. A version of the GB1-Ymbs38 protein without the 6× histidine tag (SEQ ID NO: 37) was prepared by treatment of the purified tagged protein with the THROMBIN CleanCleave™ Kit (Sigma). After an overnight incubation at 4° C. of the tagged GB1-Ymbs38 with the Thrombin CleanCleave™ resin, complete digestion was confirmed by SDS-PAGE. Any remaining tagged protein was removed by passage through the HIS-Select™ resin. Untagged protein was collected in the column flow through. The thrombin protease recognized the specific sequence of Leu-Val-Pro-(Arg or Lys)-Gly-Ser (SEQ ID NO: 23) and cleaved the protein between the Arg/Lys-Gly bond. Thrombin also was able to cleave protein at a slightly less efficient rate at Arg/Lys-Gly and Gly-Arg/Lys sequences. In both cases, the protease cleaved after the Arg/Lys residue. A Lys-Gly sequence existed in the GB1 portion of the GB1-Ymbs38 fusion protein. As shown in FIG. 19, digestion of the protein resulted in the formation of two protein fragments with approximate sizes of 10.9 kDa and 9 kDa (FIG. 19). The occurrence accounts for the appearance of two bands in the SDS-PAGE of the thrombin digested GB1-Ymbs38. The 6× histidine tag (SEQ ID NO: 37) of the GB1-Ymbs38 fusion protein was removed by thrombin cleavage at the specific recognition sequence of Leu-Val-Pro-Arg-Gly-Ser (SEQ ID NO: 39). Thrombin also was capable of cleaving the protein at the Lys-Gly sequence. The resulting SDS-PAGE gel displays two bands for the digested GB1-Ymbs38 (Lane 1: Molecular Weight Standards; Lane 2: digested GB1-Ymbs38).

In the HIS-Select Affinity Resin Binding Assay, dimerization was evident by the ability of the 6× histidine tagged (SEQ ID NO: 37) version of GB1-Ymbs38 to form "homodimers" with the untagged protein and subsequently retain the untagged protein on the nickel affinity resin. As described above, tagged and untagged proteins were pre-mixed, applied to the affinity resin, washed thoroughly to remove any unbound proteins, eluted with concentrated imidazole and analyzed by SDS-PAGE (FIG. 20). Panel A shows a 6× histidine tagged (SEQ ID NO: 37) (6× his (SEQ ID NO: 37)) version of the protein mixed with an untagged protein and incubated at 37° C. for 1 hr to allow for subunit (monomer) exchange. Panel B shows the protein mixture applied to the HIS-Select affinity resin. The histidine-tag facilitated the strong adhesion of the protein to the $Ni^{2+}$ resin. Any untagged protein that was dimerized with tagged protein also adhered to the resin, while any excess protein or untagged dimer was washed through. Panel C shows imidazole added to elute the histidine-tagged protein from the resin. The eluants were analyzed by SDS-PAGE for the presence of the untagged protein, indicative of protein dimerization.

The importance of both metal binding and the presence of an aliphatic repeat sequence to GB1-Ymbs38 dimerization were tested by this assay. Apo-GB1-Ymbs38 was prepared by the EDTA treatment method described above and the free cysteines in the Ymbs38 metal binding site were subsequently modified by iodoacetamide. Another variant of GB1-Ymbs38, in which the leucine and isoleucine residues were mutated to serine residues, was created through use of the QuikChange® Site-Directed Mutagenesis Kit (Stratagene). Each of these GB1-Ymbs38 variants included the 6× histidine tag (SEQ ID NO: 37), and each was pre-mixed with the untagged wild-type Zn(II) GB1-Ymbs38 protein for the HIS-Select Resin Binding Assay.

FIG. 21 shows the results of the HIS-Select Resin Binding assay on the GB1-Ymbs38 variants. Lane 1 is a mixture of 6× his tagged (SEQ ID NO: 37) GB1-Ymbs38 with untagged GB1-Ymbs38 before application to the affinity resin. Lanes 2, 6, 9, 12 and 15 are wash fractions. Lane 3 is an Eluant of tagged GB1-Ymbs38 with untagged GB1-Ymbs38 assay mixture. Lane 4 is an EZ Run Molecular Weight Standard (Fisher Scientific). Lane 5 is untagged GB1-Ymbs38 before application to the affinity resin. Lane 7 is an eluant of untagged GB1-Ymbs38. Lane 8 is a mixture of 6× his tagged (SEQ ID NO: 37) GB1 with untagged GB1-Ymbs38 before application to the affinity resin. Lane 10 is an eluant of tagged GB1 with untagged GB1-Ymbs38 assay mixture. Lane 11 is a mixture of 6× his tagged (SEQ ID NO: 37) apo (cysteine modified) GB1-Ymbs38 with untagged GB1-Ymbs38 before application to the affinity resin. Lane 13 is an eluant of tagged apo (cysteine modified) GB1-Ymbs38 with untagged GB1-Ymbs38 assay mixture. Lane 14 is a mixture of 6× his tagged (SEQ ID NO: 37) Leu/Ile-to-Ser mutant GB1-Ymbs38 with untagged GB1-Ymbs38 before application to the affinity resin. Lane 16 is an eluant of tagged Leu/Ile-to-Ser mutant GB1-Ymbs38 with untagged GB1-Ymbs38 assay mixture.

Five separate assays were shown on the gel, separated into groups of three lanes containing the pre-mixed protein solutions, the wash step, and the elution step, respectively. Lanes 1-3 contained the mixture of 6× histidine tagged (SEQ ID NO: 37) Zn(II) GB1-Ymbs38 with the untagged protein. The difference in size of approximately 2.2 kDa between the tagged and untagged protein allowed for sufficient separation of the corresponding bands on SDS-PAGE, with the untagged protein appearing as the lower molecular weight band. Lane 2 indicates that some of the untagged protein was lost during the wash step, but it is evident in Lane 3 that the 6× histidine tagged (SEQ ID NO: 37) version of Zn(II) GB1-Ymbs38 captured much of the untagged protein and specifically retained it on the HIS-Select™ nickel affinity resin. The result correlated with the mass spectrometry data in suggesting that the Zn(II) loaded form of GB1-Ymbs38 had the capability to dimerize, as shown in FIG. 15. Lanes 5-7 contained the corresponding assay of the untagged Zn(II) GB1-Ymbs38 protein alone, as a control, which demonstrated that the untagged protein lacked the ability to interact with the affinity resin. All of the protein was removed by the washing steps. The Ymbs38 fragment was required to be present in order for dimerization to occur, as proven by the mixture of the untagged protein with the 6× histidine tagged (SEQ ID NO: 37) GB1 (Lanes 8-10). GB1 (in this case, the lower molecular weight band on the gel, at a size of 8.4 kDa) was unable to retain the untagged Zn(II) GB1-Ymbs38, as evidenced by the presence of only GB1 in the eluant (Lane 10). Lanes 11-13 contained the steps of the untagged Zn(II) GB1-Ymbs38 and tagged apo (cysteine modified) protein assay mixture. Removal of the Zn(II) from the Ymbs38 metal binding site appeared to greatly diminish the dimer interaction, as no untagged protein was detectable in Lane 13. The result corroborated with the observed behavior of apo-GB1-Ymbs38 in the electrospray ionization mass spectrometry experiments (FIG. 18). Likewise, mutation of the hydrophobic amino acids in the proposed helical section of GB1-Ymbs38 to hydrophilic residues appeared to eliminate dimerization, even if the metal binding site was loaded with Zn(II) (Lanes 14-16). The data demonstrated that dimerization was mediated by interactions solely between the Ymbs residues, and that the extent of dimerization was affected by metal binding to the Cys-x-Cys-xxxx-Cys-x-Cys (SEQ ID NO: 38) site as well as the presence of an aliphatic repeat sequence immediately adjacent to the metal binding site.

4. Large Zone Size Exclusion Chromatography of GB1-Ymbs38

Size exclusion chromatography, electrospray ionization mass spectrometry and the affinity resin binding assay indicated that Zn(II) GB1-Ymbs38 was indeed a dimer, and that the dimerization interaction was hindered by the loss of metal and by the substitution of hydrophilic amino acids for the native hydrophobic residues. The GB1-Ymbs38 protein was therefore subjected to large zone size exclusion chromatography in order to attain a more complete assessment of the monomer-dimer equilibrium of each protein variant. Large zone chromatography enabled the elucidation of the strength of the dimer interaction by measuring the dependence of the elution volume, $V_e$, on the concentration of protein loaded onto the chromatography column.

Four variants of the GB1-Ymbs38 fusion protein were tested by this technique. Zn(II) GB1-Ymbs38, apo-GB1-Ymbs38, Zn(II) GB1-Ymbs38 Leu/Ile-to-Ser mutant and apo-GB1-Ymbs38 Leu/Ile-to-Ser mutant were each applied in 5 mL aliquots to the Shodex KW803 HPLC column equilibrated in 50 mM Tris, pH 7.8, 150 mM NaCl, 0.05% β-mercaptoethanol. Loading concentrations of the proteins varied in the range between 3 μM to 270 μM. Injections of protein at each individual concentration were repeated in triplicate. The weight average elution volume, $V_e$, of each particular loaded sample was determined from the peak value of the advancing edge from the first derivative plot of the elution profile, shown in FIG. 22. Panel A is a chromatograph showing the 280 nm absorbance trace for the large zone experiment. A 5 mL aliquot of Zn(II) CopY was loaded onto a Shodex KW 803 column (total column volume is 15 mL) equilibrated in 50 mM Tris, pH 7.8, 150 mM NaCl, 0.05% β-mercaptoethanol. Zn(II) CopY was loaded at concentrations, from the top curve going down of 142 μM, 72 μM, 38 μM, 21 μM, 11 μM, 6 μM, 3 μM, 1.4 μM, 1 μM, and 0.5 μM. Panel B shows the first derivative curves of the elution profiles from Panel A. Proteins undergoing rapid equilibrium between the monomer and dimer forms had characteristic large zone first derivative curves consisting of very sharp leading edges, (left) and diffuse trailing edges (right). The measure of the apparent molecular weight of the protein at each concentration was calculated by correlating the elution volume of the leading edge with elution volumes of known molecular weight standards.

The apparent molecular weight of each applied protein concentration were estimated by relating $V_e$ of the advancing edge to a molecular weight standard curve. As shown in FIG. 23, a shift in size from approximately 26.5 kDa at a loading concentration of 270 μM to approximately 15 kDa at a loading concentration of 3.5 μM was observed for the large zone chromatography experiment on the native Zn(II) GB1-Ymbs38 protein (diamonds in FIG. 23). The observed shift corresponded to a change from predominately dimeric protein at the higher concentrations to predominately monomeric protein at the lower concentrations, considering that the monomeric molecular weight of GB1-Ymbs38 was 12.8 kDa.

Each variant of the GB1-Ymbs38 fusion protein exhibited different behavior compared to the native protein. The change that caused the least effect on the monomer-dimer equilibrium was the mutation of the leucine and isoleucine residues to serine residues. When the mutated protein remained loaded with Zn(II), the observed shift in molecular weight was from approximately 25 kDa at a loading concentration of 260 μM to approximately 15 kDa at a loading concentration of 3.9 μM (squares in FIG. 23). Considering the standard deviation of apparent molecular weight at each loading concentration, the native Zn(II) GB1-Ymbs38 and the mutated Zn(II) GB1-Ymbs38 Leu/Ile-to-Ser protein exhibited essentially the same behavior.

The removal of Zn(II) from the metal binding site of the native GB1-Ymbs38 caused a detectable decrease in the strength of the dimerization interaction. The protein is still capable of dimerization at higher concentrations, observed as a species of approximately 22 kDa at a loading concentration of 170 μM. The observed shift in apparent molecular weight ended at a size of approximately 13 kDa at a loading concentration of 4.1 μM (triangles in FIG. 23). At each intermittent loading concentration, the apparent molecular weight of the apo (cysteine-modified) GB1-Ymbs38 protein was noticeably less than the sizes measured for the native Zn(II) protein and the mutated Zn(II) protein. Also, at the lowest loading concentration, the protein eluted at a size that was much closer to the actual monomeric molecular weight of 12.8 kDa than do either of the Zn(II)-loaded proteins. Zn(II) GB1-Ymbs38, Zn(II) GB1-Ymbs38 Leu/Ile-to-Ser mutant and apo-GB1-Ymbs38 retained the ability to dimerize, evidenced by their measurable shifts in molecular weight as the protein concentration changed. Apo-GB1-Ymbs38 Leu/Ile-to-Ser mutant exists as a monomer at all protein concentrations tested, with a maximum apparent molecular weight of 14.8 kDa at the highest concentration. [Diamonds: Zn(II) GB1-Ymbs38; squares: Zn(II) GB1-Ymbs38 Leu/Ile-to-Ser mutant; triangles: apo-GB1-Ymbs38 (cysteines are modified with iodoacetamide); circles: apo-GB1-Ymbs38 Leu/Ile-to-Ser mutant (cysteines modified)].

The most drastic change in behavior was observed when both the Zn(II) and the hydrophobic leucine and isoleucine residues were removed from the protein. Only a very slight shift in apparent molecular weight was observed for the large zone chromatography experiment on the apo (cysteine-modified) GB1Ymbs39 Leu/Ile-to-Ser mutant. An apparent size of approximately 14.8 kDa was recorded at the highest loading concentration of 132 μM, and at the lowest loading concentration of 3.8 μM, a species of approximately 12.8 kDa was detected (circles in FIG. 23). The low apparent molecular weight at 132 μM, compared to sizes between 21-23 kDa for the other protein variants at the same concentration, indicated that the protein had lost most of its affinity between monomers that allowed it to dimerize. The apo-GB1-Ymbs38 Leu/Ile-to-Ser mutant appeared to exist as a monomer at all protein concentrations tested, based on the overlap of the error bars for each sample data point. The results of the large zone size exclusion chromatography experiments, combined with the observations made through the electrospray ionization mass spectrometry and the affinity resin binding assay, indicated that the 38 C-terminal residues of CopY constituted a protein dimerization domain which operated through both metal binding and hydrophobic interactions.

The plot of the change in apparent molecular weight versus the concentration of protein loaded onto the chromatography column provided an understanding of the process that occurred during the large zone chromatography experiment. The acquired data could be further manipulated in order to calculate the equilibrium dissociation constant for the GB1-Ymbs38 dimer. The elution volume, $V_e$ was converted to the weight average partition coefficient, $\sigma_w$, which represented the fraction of solvent volume within the gel matrix that was accessible to the protein. FIG. 24 shows a plot of the weight average partition coefficient versus the log of the loaded protein concentration. The data points are the recorded experimental values of $\sigma_w$ at each loading concentration, and the solid line illustrates the best fit of the data to a monomer-dimer stoichiometric model. Non-linear least squares analysis was used to obtain the best fit according to the procedure. To verify that the data was fit to the appropriate stoichiometric model, a residual plot, which plots the difference between the observed $f_m$ and the calculated $f_m$ versus log [loaded protein], was prepared. The elution volume of each sample was converted to the weight average partition coefficient, which was plotted as a function of GB1-Ymbs38 concentration loaded onto the chromatography column. The $K_d$ value was calculated from the best fit of the data to a monomer-dimer stoichiometric model, represented on the plot as a solid line. The plot shown corresponds to one of the three large zone chromatography trials performed on the apo-GB1-Ymbs38 protein variant.

FIG. 25 shows that the residuals were distributed randomly about the line corresponding to y=0, indicating that the model represented the data correctly. The fitting of the data yielded the equilibrium association constants for each protein variant, which were subsequently converted to dissociation constants, $K_d$. Residual points were obtained by subtracting the fraction of monomer calculated by the best fit from the actual experimental value. Residuals were ploted against the log (loaded protein). The random distribution about the y=0 axis indicates that the monomer-dimer stoichiometry model used for the data fitting is an appropriate model.

Equilibrium association constants were used to calculate the Gibbs energy of assembly)($\Delta G°$) through the equation: $\Delta G° = -RT\ln K_a$. Equilibrium association and dissociation constants, and the Gibbs free energy changes are shown in Table 6 for each GB1-Ymbs38 variant. A decrease in affinity between GB1-Ymbs38 monomers occurred upon mutation of the leucine and isoleucine residues or upon the removal of Zn(II), with the Zn(II) removal resulting in a larger decrease. The combination of Zn(II) removal and mutation of the aliphatic amino acids eliminated the ability of GB1-Ymbs38 monomer to self-associate.

TABLE 6

Resolved Parameters of GB1-Ymbs38 Monomer-Dimer Equilibrium

| GB1-Ymbs38 Variant | Association constant $K_a$ (M$^{-1}$) | Dissociation constant $K_d$ (M) | Gibbs energy ($\Delta G°$) of dimerization (kcal/mol) |
|---|---|---|---|
| Zn(II)GB1-Ymbs38 | 3.7 (±0.3) × 10$^4$ | 2.8 (±0.2) × 10$^{-5}$ | −5.9 ± 0.05 |
| Zn(II)GB1-Ymbs38 Leucine mutant | 3.2 (±0.5) × 10$^4$ | 3.2 (±0.6) × 10$^{-5}$ | −5.7 ± 0.09 |
| Apo-GB1-Ymbs38 | 1.0 (±0.1) × 10$^4$ | 5.1 (±0.3) × 10$^{-5}$ | −5.4 ± 0.03 |
| Apo-GB1-Ymbs38 Leucine mutant | N/A | N/A | N/A |

Association constants are derived directly from the non-linear least squares best fit of the weight average partition coefficient versus log[loaded GB1-Ymbs38] data. Dissociation constants are calculated from the association constants by taking the reciprocal. Energies of association are calculated through the equation
$\Delta G° = -RT\ln K_a$ where R = 0.001987 kcal/K · mol and T is the temperature in Kelvin at which the experiment was carried out (277 K or 4° C.).

5. Analytical Ultracentrifugation of CopY

Analytical ultracentrifugation was utilized to confirm size exclusion data suggesting that the stable CopY dimer is disrupted upon removal of zinc. The ultracentrifugation data, as shown in FIG. 26, suggested that the samples were a heterogeneous mixture of monomers and dimers. The coordination of Zn(II) shiftsed the distribution of dimer and monomer. The Zn(II) CopY appeared to be 85%-15% dimer-monomer mixture (A) while removal of the Zn(II) to make apoCopY resulted in a shift to a mixture of 25%-75% dimer-monomer (B).

Discussion

1. Large Zone Gel Filtration Chromatography on CopY

The investigation presented herein verified the specific factors that contribute to the dimerization of CopY and revealed their energetic contributions to the strength of self-association of proteins. As the copY protein was translated, the post-translational incorporation of Zn(II) induced the correct folding of the region around the CopY metal-binding site and thereby initiated protein dimerization. Hydrophobic interactions between nearby aliphatic (Ser/Ile) amino acids contributed to the stability of the CopY dimer.

Initial characterization of the GB1-Ymbs38 fusion protein by size exclusion chromatography indicated that the protein is dimeric in nature. The fusion protein migrates with an apparent molecular weight of 22.5 kDa (FIG. 14), while the GB1 protein, without the Ymbs38 extension, migrated at approximately 10 kDa. The calculated molecular weight of GB1 is 8.4 kDa, and the fusion of the 38 CopY amino acids added an additional 4.4 kDa. The calculated molecular weight of the fusion protein, therefore, was 12.8 kDa. The GB1 protein eluted at a size that corresponded to a monomeric species, but the GB1-Ymbs38 fusion eluted at a size that was nearly double its actual molecular weight. Thus, the addition of the 38 C-terminal amino acids of CopY was sufficient to promote dimerization.

The results of frontal zone exclusion chromatography experiments provided further support to the conclusion that GB1-Ymbs38 was a dimeric protein. The elution volume of the protein increased as the concentration of the sample applied to the column decreased (FIG. 24), a behavior that is characteristic of an oligomeric protein that exists in a dynamic equilibrium between the monomeric and oligomeric forms. Frontal zone chromatography was carried out in triplicate on four variants of the GB1-Ymbs38 protein, the Zn(II) and apo (cysteine-modified) forms of the wild type protein, and the Zn(II) and the apo (cysteine-modified) forms of the Leu/Ile-to-Ser mutant protein. The absence of metal noticeably weakened the dimerization interaction. Zn(II) was removed from both the wild type and the mutated proteins by treatment with 125 mM EDTA. To prevent interaction of the cysteinyl thiols with each other or with other trace metals, iodoacetamide was introduced as a covalent modifier of the thiol groups. The apo form of the wild type GB1-Ymbs38 retained the ability to dimerize at high protein concentrations, but dissociated to monomers more readily than either of the Zn(II) loaded proteins do.

The absence of both the Zn(II) and the hydrophobic residues rendered the apoGB1-Ymbs38 Leu/Ile-to-Ser mutant unable to dimerize. The apparent molecular weight at the highest loading concentration was 14.8 kDa, considered to be essentially monomeric in nature. As concentration decreased, apparent molecular weight shifted to a final size of 12.8 kDa. The behavior of this particular variant of GB1-Ymbs38 confirmed that the dimerization mechanism was reliant on both hydrophobic interactions and Zn(II) binding to the cysteine rich metal binding site. The metal binding appeared to be the more critical factor, as dimerization was weakened more by the removal of Zn(II) than by the mutation of the leucine and isoleucine residues.

FIG. 24 shows a plot of the weight average partition coefficient versus the log of the loaded protein concentration of the apoGB1-Ymbs38 protein variant. Data plotted in this manner were analyzed by non-linear least squares analysis in order to obtain an equilibrium association constant, $K_a$, that described the strength of the measured protein dimerization. Dissociation constants, $K_d$, obtained by taking the reciprocal of $K_a$, were a measure of protein affinity with respect to protein concentration. Table 1 expresses both the $K_a$ and $K_d$ values. Dimers of Zn(II) GB1-Ymbs38 associated with the highest affinity of all the protein variants, with a $K_d$ of 2.8× 10-5M (28 Affinities progressively weakened with the mutation of hydrophobic residues, the removal of Zn(II) from the metal binding site, and the combination of both, respectively.

Another manner of expressing affinities is to report the standard Gibbs free energy of association. Standard Gibbs free energies for the GB1-Ymbs38 variants range in magnitude from the largest at −5.9 kcal/mol for Zn(II) GB1-Ymbs38 to the smallest at −5.4 kcal/mol for apoGB1-Ymbs38 Leu/Ile-to-Ser mutant. Large zone chromatography was limited to the measurement of associating proteins with standard Gibbs free energies of approximately −10 kcal/mol at the greatest. Typical energies reported for proteins of average association strength were in the range of −7 to −8 kcal/mol. The energy of the strongest GB1-Ymbs38 association of −5.9 kcal/mol was slightly lower than average.

This investigation demonstrated that -CxCxxxxCxC-(SEQ ID NO: 38) sites in low (less than 2%) total cysteine content proteins can serve as zinc or copper binding sites. Over 1000 sequences containing the -CxCx$_{(4-6)}$CxC (SEQ ID NO: 1) were screened and divided into loose categories. There were clear distinctions between the cysteine rich membrane proteins, toxins, metallothioneins and the copper binding regulatory proteins with the -CxCxxxxCxC- (SEQ ID NO: 38) motif(s), therefore these were excluded from any subsequent analyses. All proteins with more than one -CxCx(4-6)CxC- (SEQ ID NO: 1), such as Ace1, Amt1 and Mac1, though known Cu(I) binding proteins, also were excluded. The resulting collection of proteins was screened to ensure that the total cysteine content was below 5%. Those with more than 2% cysteine were considered likely to be heavily disulfide cross-linked or metallothionein type proteins, and thus were eliminated. The remaining proteins were broadly gathered into clusters based on homology to each other.

Several features of the sequence motif and surrounding sequences suggested a commonality of structure and plausibly function. Table 7 shows a partial listing of sequences, which highlights a few families containing the motif that were investigated, although this is not a complete list of the sequences that contain the motif. The numbering of the motif is from the first cysteine on the N-terminal side of the sequence, which is position 1, the residue is position 2 and so forth across the motif, in which the C's are in positions 1,3, 8 and 10. The displayed motif is limited to those with only 4 residues between the middle two cysteines. Position 4 is predominately an aliphatic residue (V, L, I, P). When the position is not aliphatic, then its symmetry position in the motif, 7, is aliphatic. Typically, positions 11-13 contain a positive charge bearing K, R or, less frequently, an H. Usually, these are in pairs.

TABLE 7

CxCxxxxCxC-SEQ ID NO: 38) Motifs across biology*

Bacterial homologs of *Enteroccocus hirae* CopY, copper sensors-regulators

*E. hirae* (CopY)
LPSHICAKRVGATIADLVEEATLTQEDIQQIMKQLNKKEPVETIICNCIPGQCECKKQ
(SEQ ID NO: 24)

*Lactobacillus sakei*
EHLCGMKKGQTLAALIDQTTLSQTDILQLQQLLTAKANTAPEKVACDCLPNKCDCEKEE
(SEQ ID NO: 25)

*Streptococcus Mutans*
SRICVTKHQALIRHLVEETPMTLSDIEKLEALLLSKKANAVPEVKCNCIVGQCSCYEHL
(SEQ ID NO: 26)

Uncharacterized homologous cluster of plant proteins

*Arabidopsis thaliana*
MLFSNKVNSLTEQVSRLDIDDNDMGLGGSETMECKCGMPLCICVAPP
(SEQ ID NO: 27)

*Zea mays*
HADNPVSAGSISGAADSPSGLSLGKEDDSSPMKNSTVQSTAALIECKCGMPLCICEAPK
(SEQ ID NO: 28)

*Oryza sativa*
GVGNAGSPGSVSSAADSPSGLNLGEDDASSPMKNSAPHSAPAVIECKCGMPLCICEAPK
(SEQ ID NO: 29)

Glutamate decarboxylase 2 family, dimers with regulatory links to zinc level [26]

*Homo sapiens*
AWCQVAQKFTGGIGNKLCALLYGDAEKPAESGGSQPPRAAARKAACACDQKPCSCSKVD
(SEQ ID NO: 30)

*Rattus norvegicus*
AWCQVAQKFTGGIGNKLCALLYGDSEKPAESGGSVTSRAATRKVACTCDQKPCSCPKGD
(SEQ ID NO: 31)

*Mus musculus*
AWCQVAQKFTGGIGNKLCALLYGDSGKPAEGGGSVTSRAATGKVACTCDQKPCNCPKGD
(SEQ ID NO: 32)

TABLE 7-continued

CxCxxxxCxC-SEQ ID NO: 38) Motifs across biology*

Uncharacterized homologous cluster, oxidative stress related[27]

*Homo sapiens*
TSVPRLPSESKKEDSSDATQVPQASLKASDLSDFQSVSKLNQGKPCTCIGKECQCKRWH
(SEQ ID NO: 33)

*Rattus norvegicus*
SSVLRLPSESKTEELSDATQVSPESETANDLSDFQSVSKLSQGKPCVCVGKACQCKRWH
(SEQ ID NO: 34)

*Mus musculus*
SSVLRLPSESKTEELSDATQVSQESETANDLSDFQSVSKLSQGKPCVCVGKECQCKRWH
(SEQ ID NO: 35)

*X. tropicalis*
SGASPSETSSETIKNASISLASPASLTASQPSDFQSVSILGTAAECTCDEKECQCKNCW
(SEQ ID NO: 36)

*The highlight show hydrophobic residues, frequently as aliphatic repeats.
The cysteines are underlined on the right side and blocked by vertical lines.

In conclusion, this investigation demonstrated that CopY dimerization occurred through a combination of both metal binding to the cysteine sequence motif and hydrophobic interactions through a region of the protein rich in aliphatic amino acids. The results also demonstrated that Zn(II) plays an important role in pre-stabilizing the CopY metal binding site for the correct incorporation of Cu(I). The use of a metal to facilitate the binding of a subsequent metal is an observation that has recently become more widespread in metalloprotein research. The mammalian copper metallothionein and the *Arabidopsis thaliana* molybdopterin proteins have also been shown to incorrectly bind the metal that is necessary for their biological functions if an initial, pre-stabilizing, metal is not first bound to the metal binding site.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

SEQUENCE LISTING

```
<160> NUMBER OF SEQ ID NOS: 41

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (4)..(9)
<223> OTHER INFORMATION: Any amino acid and this region may encompass
      4-6 residues
<220> FEATURE:
<221> NAME/KEY: MOD_RES
<222> LOCATION: (11)
<223> OTHER INFORMATION: Any amino acid

<400> SEQUENCE: 1

Cys Xaa Cys Xaa Xaa Xaa Xaa Xaa Xaa Cys Xaa Cys
  1               5                  10

<210> SEQ ID NO 2
<211> LENGTH: 38
<212> TYPE: PRT
<213> ORGANISM: Artificial Sequence
<220> FEATURE:
<223> OTHER INFORMATION: Description of Artificial Sequence: Synthetic
```

```
                                     -continued
        peptide

<400> SEQUENCE: 2

Ala Thr Leu Thr Gln Glu Asp Ile Gln Gln Ile Met Lys Gln Leu Asn
 1               5                  10                  15

Lys Lys Glu Pro Val Glu Thr Ile Glu Cys Asn Cys Ile Pro Gly Gln
                20                  25                  30

Cys Glu Cys Lys Lys Gln
            35

<210> SEQ ID NO 3
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Ser Gln Thr Asp Ile Leu Gln Leu Gln Gln Leu Leu Thr Ala Lys
 1               5                  10                  15

Ala Ala Thr Ala Pro Glu Lys Val Ala Cys Asp Cys Leu Pro Asn Lys
                20                  25                  30

Cys Asp Cys Glu Lys Glu
            35

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Thr Leu Ser Asp Ile Glu Lys Leu Glu Ala Leu Leu Leu Ser Lys
 1               5                  10                  15

Lys Ala Asn Ala Val Pro Glu Val Lys Cys Asn Cys Ile Val Gly Gln
                20                  25                  30

Cys Ser Cys Tyr Glu His
            35

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Leu Thr Glu Gln Val Ser Arg Leu Asp Ile Asp Asp Asn Asp Met
 1               5                  10                  15

Gly Leu Gly Gly Ser Glu Thr Met Glu Cys Lys Cys Gly Met Pro Leu
                20                  25                  30

Cys Ile Cys Val Ala Pro
            35

<210> SEQ ID NO 6
<211> LENGTH: 38
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 6

Leu Ser Leu Gly Lys Glu Asp Asp Ser Ser Pro Met Lys Asn Ser Thr
1               5                   10                  15

Val Gln Ser Thr Ala Ala Leu Ile Glu Cys Lys Cys Gly Met Pro Leu
            20                  25                  30

Cys Ile Cys Glu Ala Pro
        35

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Asn Leu Gly Glu Asp Asp Ala Ser Ser Pro Met Lys Asn Ser Ala
1               5                   10                  15

Phe His Ser Ala Pro Ala Val Ile Glu Cys Lys Cys Gly Met Pro Leu
            20                  25                  30

Cys Ile Cys Glu Ala Pro
        35

<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Tyr Gly Asp Ala Glu Lys Pro Ala Glu Ser Gly Gly Ser Gln Pro
1               5                   10                  15

Pro Arg Ala Ala Ala Arg Lys Ala Ala Cys Ala Cys Asp Gln Lys Pro
            20                  25                  30

Cys Ser Cys Ser Lys Val
        35

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Tyr Gly Asp Ser Gly Lys Pro Ala Glu Gly Gly Gly Ser Val Thr
1               5                   10                  15

Ser Arg Ala Ala Thr Gly Lys Val Ala Cys Thr Cys Asp Gln Lys Pro
            20                  25                  30

Cys Asn Cys Pro Lys Gly
        35

<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 10

Val Pro Gln Ala Ser Leu Lys Ala Ser Asp Leu Ser Asp Phe Gln Ser
 1               5                  10                  15

Val Ser Lys Leu Asn Gln Gly Lys Pro Cys Thr Cys Ile Gly Lys Glu
            20                  25                  30

Cys Gln Cys Lys Arg Trp
         35

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ser Pro Glu Ser Leu Thr Ala Asn Asp Leu Ser Asp Phe Gln Ser
 1               5                  10                  15

Val Ser Lys Leu Ser Gln Gly Lys Pro Cys Val Cys Val Gly Lys Ala
            20                  25                  30

Cys Gln Cys Lys Arg Trp
         35

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ser Pro Ala Ser Leu Thr Ala Ser Gln Pro Ser Asp Phe Gln Ser
 1               5                  10                  15

Val Ser Ile Leu Gly Thr Ala Ala Glu Cys Thr Cys Asp Glu Lys Glu
            20                  25                  30

Cys Gln Cys Lys Asn Cys
         35

<210> SEQ ID NO 13
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(285)

<400> SEQUENCE: 13 cat atg cag tat aaa ctg att ctg aac ggc aaa ccc ctg aaa ggc gaa    48
His Met Gln Tyr Lys Leu Ile Leu Asn Gly Lys Pro Leu Lys Gly Glu
 1               5                  10                  15 acc acc acc gaa gcg gtg gat gcg gcg acc gcg gaa aaa gtg ttt aaa    96
Thr Thr Thr Glu Ala Val Asp Ala Ala Thr Ala Glu Lys Val Phe Lys
            20                  25                  30 cag tat gcg aat gat aat ggc gtg gat ggc gaa tgg acc tat gat gat   144
Gln Tyr Ala Asn Asp Asn Gly Val Asp Gly Glu Trp Thr Tyr Asp Asp
         35                  40                  45 gcg acc aaa acc ttt acc gtg acc gaa gcg caa ttg acc cag gaa gat   192

```
Ala Thr Lys Thr Phe Thr Val Thr Glu Ala Gln Leu Thr Gln Glu Asp
         50                  55                  60 att cag cag att atg aaa caa ttg aat aaa aaa gaa ccg gtg gaa acc      240
Ile Gln Gln Ile Met Lys Gln Leu Asn Lys Lys Glu Pro Val Glu Thr
 65                  70                  75                  80 att gaa tgc aac tgc att ccg ggc cag tgc gaa tgc aaa aaa cag          285
Ile Glu Cys Asn Cys Ile Pro Gly Gln Cys Glu Cys Lys Lys Gln
                 85                  90                  95 taatgatca                                                            294
```

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Asn Cys Leu Pro Gly Gln Cys His Cys
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)
<223> OTHER INFORMATION: Any amino acid
<220> FEATURE:
<221> NAME/KEY: MOD_RES
<222> LOCATION: (11)
<223> OTHER INFORMATION: Any amino acid

<400> SEQUENCE: 15

Cys Xaa Cys Pro Xaa Xaa Xaa Pro Xaa Cys Xaa Cys
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Thr Cys Pro Ser Ile Asp Ala Cys Thr Cys
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 17

Cys Lys Cys Arg Asp Ser Pro Phe Cys Gly Cys
  1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (10)
<223> OTHER INFORMATION: Any amino acid

<400> SEQUENCE: 18

Cys Xaa Cys Xaa Xaa Gln Lys Pro Cys Xaa Cys
  1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Gln Cys Gly Pro Lys Phe Pro Glu Cys Asn Cys
  1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Asp Cys Arg Pro Gly Gln Lys Lys Cys Thr Cys
  1               5                  10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Asp Cys Lys Asn Asp Ala Asn Cys Asp Cys
  1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                                    peptide

<400> SEQUENCE: 22

Cys Gln Cys Pro Ala Val Val Cys Cys Arg Cys
 1               5                  10

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Arg or Lys

<400> SEQUENCE: 23

Leu Val Pro Xaa Gly Ser
 1               5

<210> SEQ ID NO 24
<211> LENGTH: 58
<212> TYPE: PRT
<213> ORGANISM: Enteroccocus hirae

<400> SEQUENCE: 24

Leu Phe Ser His Ile Cys Ala Lys Arg Val Gly Ala Thr Ile Ala Asp
 1               5                  10                  15

Leu Val Glu Glu Ala Thr Leu Thr Gln Glu Asp Ile Gln Gln Ile Met
             20                  25                  30

Lys Gln Leu Asn Lys Lys Glu Pro Val Glu Thr Ile Glu Cys Asn Cys
         35                  40                  45

Ile Pro Gly Gln Cys Glu Cys Lys Lys Gln
     50                  55

<210> SEQ ID NO 25
<211> LENGTH: 59
<212> TYPE: PRT
<213> ORGANISM: Lactobacillus sakei

<400> SEQUENCE: 25

Glu His Leu Cys Gly Met Lys Lys Gly Gln Thr Leu Ala Ala Leu Ile
 1               5                  10                  15

Asp Gln Thr Thr Leu Ser Gln Thr Asp Ile Leu Gln Leu Gln Gln Leu
             20                  25                  30

Leu Thr Ala Lys Ala Ala Thr Ala Pro Glu Lys Val Ala Cys Asp Cys
         35                  40                  45

Leu Pro Asn Lys Cys Asp Cys Glu Lys Glu Glu
     50                  55

<210> SEQ ID NO 26
<211> LENGTH: 59
<212> TYPE: PRT
<213> ORGANISM: Streptococcus mutans

<400> SEQUENCE: 26

Ser Arg Ile Cys Val Thr Lys His Gln Ala Leu Ile Arg His Leu Val
 1               5                  10                  15

Glu Glu Thr Pro Met Thr Leu Ser Asp Ile Glu Lys Leu Glu Ala Leu
             20                  25                  30

Leu Leu Ser Lys Lys Ala Asn Ala Val Pro Glu Val Lys Cys Asn Cys
```

```
                    35                  40                  45
Ile Val Gly Gln Cys Ser Cys Tyr Glu His Leu
         50                  55

<210> SEQ ID NO 27
<211> LENGTH: 47
<212> TYPE: PRT
<213> ORGANISM: Arabidopsis thaliana

<400> SEQUENCE: 27

Met Leu Phe Ser Asn Lys Val Asn Ser Leu Thr Glu Gln Val Ser Arg
  1               5                  10                  15

Leu Asp Ile Asp Asp Asn Asp Met Gly Leu Gly Ser Glu Thr Met
             20                  25                  30

Glu Cys Lys Cys Gly Met Pro Leu Cys Ile Cys Val Ala Pro Pro
         35                  40                  45

<210> SEQ ID NO 28
<211> LENGTH: 59
<212> TYPE: PRT
<213> ORGANISM: Zea mays

<400> SEQUENCE: 28

His Ala Asp Asn Pro Val Ser Ala Gly Ser Ile Ser Gly Ala Ala Asp
  1               5                  10                  15

Ser Phe Ser Gly Leu Ser Leu Gly Lys Glu Asp Asp Ser Ser Pro Met
             20                  25                  30

Lys Asn Ser Thr Val Gln Ser Thr Ala Ala Leu Ile Glu Cys Lys Cys
         35                  40                  45

Gly Met Pro Leu Cys Ile Cys Glu Ala Pro Lys
     50                  55

<210> SEQ ID NO 29
<211> LENGTH: 59
<212> TYPE: PRT
<213> ORGANISM: Oryza sativa

<400> SEQUENCE: 29

Gly Val Gly Asn Ala Gly Ser Pro Gly Ser Val Ser Ser Ala Ala Asp
  1               5                  10                  15

Ser Phe Ser Gly Leu Asn Leu Gly Glu Asp Asp Ala Ser Ser Pro Met
             20                  25                  30

Lys Asn Ser Ala Phe His Ser Ala Pro Ala Val Ile Glu Cys Lys Cys
         35                  40                  45

Gly Met Pro Leu Cys Ile Cys Glu Ala Pro Lys
     50                  55

<210> SEQ ID NO 30
<211> LENGTH: 59
<212> TYPE: PRT
<213> ORGANISM: Homo sapiens

<400> SEQUENCE: 30

Ala Trp Cys Gln Val Ala Gln Lys Phe Thr Gly Gly Ile Gly Asn Lys
  1               5                  10                  15

Leu Cys Ala Leu Leu Tyr Gly Asp Ala Glu Lys Pro Ala Glu Ser Gly
             20                  25                  30

Gly Ser Gln Pro Pro Arg Ala Ala Ala Arg Lys Ala Ala Cys Ala Cys
         35                  40                  45

Asp Gln Lys Pro Cys Ser Cys Ser Lys Val Asp
```

```
<210> SEQ ID NO 31
<211> LENGTH: 59
<212> TYPE: PRT
<213> ORGANISM: Rattus norvegicus

<400> SEQUENCE: 31

Ala Trp Cys Gln Val Ala Gln Lys Phe Thr Gly Gly Ile Gly Asn Lys
1               5                   10                  15

Leu Cys Ala Leu Leu Tyr Gly Asp Ser Glu Lys Pro Ala Glu Ser Gly
            20                  25                  30

Gly Ser Val Thr Ser Arg Ala Ala Thr Arg Lys Val Ala Cys Thr Cys
        35                  40                  45

Asp Gln Lys Pro Cys Ser Cys Pro Lys Gly Asp
    50                  55

<210> SEQ ID NO 32
<211> LENGTH: 59
<212> TYPE: PRT
<213> ORGANISM: Mus musculus

<400> SEQUENCE: 32

Ala Trp Cys Gln Val Ala Gln Lys Phe Thr Gly Gly Ile Gly Asn Lys
1               5                   10                  15

Leu Cys Ala Leu Leu Tyr Gly Asp Ser Gly Lys Pro Ala Glu Gly Gly
            20                  25                  30

Gly Ser Val Thr Ser Arg Ala Ala Thr Gly Lys Val Ala Cys Thr Cys
        35                  40                  45

Asp Gln Lys Pro Cys Asn Cys Pro Lys Gly Asp
    50                  55

<210> SEQ ID NO 33
<211> LENGTH: 59
<212> TYPE: PRT
<213> ORGANISM: Homo sapiens

<400> SEQUENCE: 33

Thr Ser Val Pro Arg Leu Pro Ser Glu Ser Lys Lys Glu Asp Ser Ser
1               5                   10                  15

Asp Ala Thr Gln Val Pro Gln Ala Ser Leu Lys Ala Ser Asp Leu Ser
            20                  25                  30

Asp Phe Gln Ser Val Ser Lys Leu Asn Gln Gly Lys Pro Cys Thr Cys
        35                  40                  45

Ile Gly Lys Glu Cys Gln Cys Lys Arg Trp His
    50                  55

<210> SEQ ID NO 34
<211> LENGTH: 59
<212> TYPE: PRT
<213> ORGANISM: Rattus norvegicus

<400> SEQUENCE: 34

Ser Ser Val Leu Arg Leu Pro Ser Glu Ser Lys Thr Glu Glu Leu Ser
1               5                   10                  15

Asp Ala Thr Gln Val Ser Pro Glu Ser Leu Thr Ala Asn Asp Leu Ser
            20                  25                  30

Asp Phe Gln Ser Val Ser Lys Leu Ser Gln Gly Lys Pro Cys Val Cys
        35                  40                  45

Val Gly Lys Ala Cys Gln Cys Lys Arg Trp His
```

```
                50                  55

<210> SEQ ID NO 35
<211> LENGTH: 59
<212> TYPE: PRT
<213> ORGANISM: Mus musculus

<400> SEQUENCE: 35

Ser Ser Val Leu Arg Leu Pro Ser Glu Ser Lys Thr Glu Leu Ser
1               5                   10                  15

Asp Ala Thr Gln Val Ser Gln Glu Ser Leu Thr Ala Asn Asp Leu Ser
                20                  25                  30

Asp Phe Gln Ser Val Ser Lys Leu Ser Gln Gly Lys Pro Cys Val Cys
            35                  40                  45

Val Gly Lys Glu Cys Gln Cys Lys Arg Trp His
        50                  55

<210> SEQ ID NO 36
<211> LENGTH: 59
<212> TYPE: PRT
<213> ORGANISM: Xenopus tropicalis

<400> SEQUENCE: 36

Ser Gly Ala Ser Pro Ser Glu Thr Ser Ser Glu Thr Ile Lys Asn Ala
1               5                   10                  15

Ser Ile Ser Leu Ala Ser Pro Ala Ser Leu Thr Ala Ser Gln Pro Ser
                20                  25                  30

Asp Phe Gln Ser Val Ser Ile Leu Gly Thr Ala Ala Glu Cys Thr Cys
            35                  40                  45

Asp Glu Lys Glu Cys Gln Cys Lys Asn Cys Trp
        50                  55

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 37

His His His His His His
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (4)..(7)
<223> OTHER INFORMATION: Any amino acid
<220> FEATURE:
<221> NAME/KEY: MOD_RES
<222> LOCATION: (9)
<223> OTHER INFORMATION: Any amino acid

<400> SEQUENCE: 38

Cys Xaa Cys Xaa Xaa Xaa Xaa Cys Xaa Cys
```

```
<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Val Pro Arg Gly Ser
 1               5

<210> SEQ ID NO 40
<211> LENGTH: 95
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Met Gln Tyr Lys Leu Ile Leu Asn Gly Lys Pro Leu Lys Gly Glu
 1               5                  10                  15

Thr Thr Thr Glu Ala Val Asp Ala Ala Thr Ala Glu Lys Val Phe Lys
                20                  25                  30

Gln Tyr Ala Asn Asp Asn Gly Val Asp Gly Glu Trp Thr Tyr Asp Asp
            35                  40                  45

Ala Thr Lys Thr Phe Thr Val Thr Glu Ala Gln Leu Thr Gln Glu Asp
        50                  55                  60

Ile Gln Gln Ile Met Lys Gln Leu Asn Lys Lys Glu Pro Val Glu Thr
65                  70                  75                  80

Ile Glu Cys Asn Cys Ile Pro Gly Gln Cys Glu Cys Lys Lys Gln
                85                  90                  95

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (4)..(8)
<223> OTHER INFORMATION: Any amino acid
<220> FEATURE:
<221> NAME/KEY: MOD_RES
<222> LOCATION: (10)
<223> OTHER INFORMATION: Any amino acid

<400> SEQUENCE: 41

Cys Xaa Cys Xaa Xaa Xaa Xaa Xaa Cys Xaa Cys
 1               5                  10
```

What is claimed is:

1. A method of constructing protein multimers, comprising:

1) providing a plurality of proteins comprising a heterologous short dimerization or multimerization promoting peptide or peptides, wherein said short dimerization or multimerization promoting peptide or peptides possess (es) a metal binding loop motif selected from the group consisting of CxCxxxxCxC (SEQ ID NO: 38), CxCxxxxxCxC (SEQ ID NO: 41) and CxCxxxxxxCxC (SEQ ID NO: 1) and hydrophobic amino acids that repeat before and/or after said metal binding loop motif about every 3 or 4 amino acids for at least two, three or four times;

2) providing a metal; and
3) mixing the plurality of proteins and the metal so that said proteins self-assemble to form at least one protein structure selected from the group consisting of homo-dimers, hetero-dimers and multimers.

2. The method according to claim 1, wherein the metal is selected from the group consisting of zinc [Zn(II)] and copper [Cu(I)].

3. The method according to claim 1, wherein the metal binding loop motif is CxCxxxxCxC (SEQ ID NO: 38).

4. The method according to claim 1, wherein the metal binding loop motif is CxCxxxxxCxC (SEQ ID NO: 41).

5. The method according to claim 1, wherein the metal binding loop motif is CxCxxxxxxCxC (SEQ ID NO: 1).

6. The method according to claim 1, wherein the hydrophobic amino acids are selected from the group consisting of valine, isoleucine, proline, alanine, methionine, tyrosine and phenylalanine.

7. The method according to claim 1, wherein the hydrophobic amino acids comprise at least one synthetic hydrophobic residue.

8. The method according to claim 1, wherein said peptide or peptides comprise(s) ATLTQEDIQQIMKQLNKKEPVETIECNCIPGQCECKKQ (SEQ ID NO: 2).

9. The method according to claim 2, wherein the metal is zinc [Zn(II)].

10. The method according to claim 2, wherein the metal is copper [Cu(I)].

* * * * *

UNITED STATES PATENT AND TRADEMARK OFFICE
CERTIFICATE OF CORRECTION

PATENT NO. : 8,163,521 B2
APPLICATION NO. : 12/912424
DATED : April 24, 2012
INVENTOR(S) : Charles Dameron It is certified that error appears in the above-identified patent and that said Letters Patent is hereby corrected as shown below:

Column 29, line 11, "from" should read --form--.

Column 35, line 9, " $A_{230}(r)=A_{230}(0)\exp[M_A(1-\sigma_A\rho_s)\omega^2 r^2/(2RT)]1 \quad (1)$ " should read -- $A_{230}(r) = A_{230}(0) \exp[M_A(1 - v_A\rho_s)\omega^2 r^2/(2RT)]\ (1)$ --.

Column 41, "Zn(H)" should read --Zn(II)--.
Column 42, line 65, "(28 Affinities" should read --(28μM). Affinities--.
Column 45, SEQUENCE LISTING,
"<160> NUMBER OF SEQ ID NOS: 41

<210> SEQ ID NO 1"
should read
--<160> NUMBER OF SEQ ID NOS: 41
  <170> PatentIn. Ver. 3.3
  <210> SEQ ID NO 1--.

Signed and Sealed this
Twenty-fourth Day of July, 2012

David J. Kappos
*Director of the United States Patent and Trademark Office*